(12) United States Patent
Ohnuma et al.

(10) Patent No.: US 8,546,452 B2
(45) Date of Patent: Oct. 1, 2013

(54) S1P₃ RECEPTOR ANTAGONIST

(75) Inventors: Shin-ya Ohnuma, Chuo-ku (JP);
Takeshi Hasegawa, Fukushima (JP);
Tomoyuki Sada, Saitama (JP)

(73) Assignee: TOA Eiyo Ltd., Tokyo (JP)

( * ) Notice: Subject to any disclaimer, the term of this patent is extended or adjusted under 35 U.S.C. 154(b) by 1121 days.

(21) Appl. No.: 12/088,861

(22) PCT Filed: Oct. 11, 2006

(86) PCT No.: PCT/JP2006/320296
§ 371 (c)(1),
(2), (4) Date: Apr. 1, 2008

(87) PCT Pub. No.: WO2007/043568
PCT Pub. Date: Apr. 19, 2007

(65) Prior Publication Data
US 2009/0170895 A1   Jul. 2, 2009

(30) Foreign Application Priority Data

Oct. 12, 2005 (JP) ................ 2005-298111

(51) Int. Cl.
*A01N 37/52* (2006.01)
*A61K 31/155* (2006.01)
*C07C 257/00* (2006.01)

(52) U.S. Cl.
USPC ........................... 514/632; 564/226

(58) Field of Classification Search
USPC ........................... 514/632; 564/226
See application file for complete search history.

(56) References Cited

FOREIGN PATENT DOCUMENTS

| DE | 27 24 819 A1 | 12/1978 |
|---|---|---|
| DE | 4114543 A1 * | 11/1992 |
| EP | 0 212 753 A1 | 3/1987 |
| JP | 54-3071 | 1/1979 |
| JP | 62-45568 | 2/1987 |
| JP | 2002-212070 | 7/2002 |
| JP | 2002-332278 | 11/2002 |
| JP | 2003-137894 | 5/2003 |
| JP | 2005-112721 | 4/2005 |
| JP | 2005-247691 | 9/2005 |
| WO | WO 9219588 A1 * | 11/1992 |
| WO | WO 02/064616 A2 | 8/2002 |
| WO | WO 03/040097 A1 | 5/2003 |
| WO | WO 03/062392 A2 | 7/2003 |
| WO | 2006/063033 A2 | 6/2006 |

OTHER PUBLICATIONS

Wilson et al. "Arylamidrazones as Novel Corticotropin Releasing Factor Receptor Antagonist" Journal of Medicinal Chemistry, May 2002, vol. 45, No. 11, pp. 2123-2126.*
Simiand et al. "In vivo characterization of the CRF-1 receptor antagonist SSR125543A as potential treatment for stress-related disorders", Neuroscience Meetion, San Diego, CA: Society for Neuroscience, 2001, abstract, 413.10.*

Shivanyuk A. F. et al., "Phenyl Imino-Ethoxalyl Chloride, Diphenyl OX-Imidoil Chloride and Their Reactions", Organic Chemical, vol. 45, No. 7, pp. 624-628, 1979.
Attaby F. A. et al., "Reactions With Hydraziodoyl Halides (V): Synthesis of Some Amidrazones, Hydrazides, Pyrazoles and Pyrazolo[3,4-d]Pyridazine Derivatives", Arch. Pharm. Res. vol. 13, No. 4, pp. 314-318, 1990.
Tiziana B. et al, "New Access to 2-(Arylazo)-, 2-(Arylhydrazo)-, and 2-Aminoindoles,-Benzofurans, and -Thianaphtenes", J. Org. Chem., vol. 53, No. 6, pp. 1309-1312, 1988.
Dean M. Wilson, et al., "Arylamidrazones as Novel Corticotropin Releasing Factor Receptor Antagonists" Journal of Medicinal Chemistry, vol. 45, No. 11, Apr. 26, 2002, pp. 2123-2126.
Menq-Jer Lee, et al. "Vascular Endothelial Cell Adherens Junction Assembly and Morphogenesis Induced by Sphingosine-1-Phosphate", Cell, vol. 99, Oct. 29, 1999. pp. 301-312.
Susan Pyne, et al. "Sphingosine 1-phosphate signaling via the endothelial differentiation gene family of G-protein-coupled receptors", Pharmacology & Therapeutics, vol. 88, 2000. pp. 115-131.
Ji H. Paik, et al. "Sphingosine 1-Phosphate-induced Endothelial Cell Migration Requires the Expression of EDG-1 and EDG-3 Receptors and RHO-dependent Activation of $\aleph_v\beta_3$- and $\beta_1$—containing Intergrins", The Journal of Biological Chemistry, vol. 276, No. 15, Apr. 13, 2001. pp. 11830-11837.
Feng Liu, et al. "Differential regulation of Sphingosine-1-Phosphate- and VEGF-Induced Endothelial Cell Chemotaxis", American Journal of Respiratory Cell and Molecular Biology, vol. 24, 2001. pp. 711-719.
Tamar Licht, et al. "Induction of pro-angiogenic signaling by a synthetic peptide derived from the second intracellular loop of $S1P_3$(EDG3)", Hemostasis, Thrombosis, and Vascular Biology, Blood, vol. 102, No. 6, Sep. 15, 2003. pp. 2099-2107.
Tracee Scalise Panetti, "Differential effects of sphingosine 1-phosphate and lysophosphatidic acid on endothelial cells", Biochimica et Biophysica Acta, vol. 1582, 2002. pp. 190-196.
Yanhua Hu, et al. "Inhibition of Neointima Hyperplasia of Mouse Vein Grafts by Locally Applied Suramin", Circulation published by the American Heart Association, vol. 100, Aug. 24, 1999. pp. 861-868.

(Continued)

*Primary Examiner* — Kendra D Carter
(74) *Attorney, Agent, or Firm* — Oblon, Spivak, McClelland, Maier & Neustadt, L.L.P.

(57) ABSTRACT

The present invention relates to arylamidrazone derivatives having an antagonistic action against $S1P_3$ receptors represented by the following formula (1) or a pharmaceutically acceptable salt thereof:

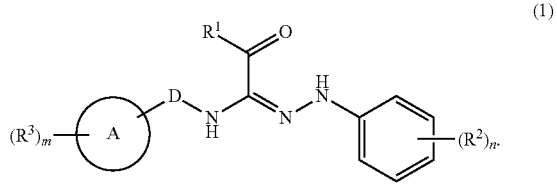

19 Claims, No Drawings

(56) References Cited

OTHER PUBLICATIONS

Yujiro Asada, et al. "Suramin inhibits intimal thickening following intimal injury in the rabbit aorta in vivo", Cardiovascular Research published by Elsevier, vol. 28, 1994. pp. 1166-1169.

Nobuko Nakajima, et al. "Expression and characterization of Edg-1 receptors in rat cardiomyocytes: Calcium deregulation in response to sphingosine 1-phosphate", European Journal of Biochemistry, vol. 267, 2000. pp. 5679-5686.

David Mazurais, et al. "Cell Type-specific Localization of Human Cardian S1P Receptors", The Journal of Histochemistry & Cytochemistry, vol. 50, No. 5, 2002. pp. 661-669.

Frederic Coussin, et al. "Comparison of Sphingosine-1-Phosphate-Induced Intracellular Signaling Pathways in Vascular Smooth Muscles: Differential Role in Vasoconstriction", Circulation Research published by the American Heart Association, vol. 91, Jul. 26, 2002. pp. 151-157.

Masahiko Tosaka, et al. "Sphingosine 1-Phosphate Contracts Canine Basilar Arteries In Vitro and In Vivo: Possible Role in Pathogenesis of Cerebral Vasospasm", Stroke published by the American Heart Association, vol. 32, Dec. 2001. pp. 2913-2919.

Salvatore Salomone, et al. "$S1P_3$ receptors mediate the potent constriction of cerebral arteries by sphingosine-1-phosphate", European Journal of Pharmacology, vol. 469, 2003. pp. 125-134.

Keiji Oi, et al. "Remnant Lipoproteins from Patients with Sudden Cardiac Death Enhance Coronary Vasospastic Activity Through Upregulation of Rho-Kinase", Arterioscler, Thrombosis and Vascular Biology published by the American Heart Association, vol. 24, May 2004. pp. 918-922.

Hiroyuki Okamoto, et al. "EDG3 is a Functional Receptor Specific for Sphingosine 1-Phosphate and Sphingosylphosphorylcholine with Signaling Characteristics Distinct from EDG1 and AGR16", Biochemical and Biophysical Research Communication, vol. 260, No. 1, 1999. pp. 203-208.

Angela Bischoff, et al. "Sphingosine-1-phosphate and sphingosylphosphorylcholine constrict renal and mesenteric microvessels in vitro", British Journal of Pharmacology, vol. 130, 2000. pp. 1871-1877.

Susumi Katsuma, et al. "Signalling mechanisms in sphingosine 1-phosphate-promoted mesangial cell proliferation", Genes to Cells, vol. 7, 2002. pp. 1217-1230.

Masashi Fukagawa, et al. "Role of Sphingolipid and possibility for development of new antifibrosis drug:", Cardiology Department Tokyo Teishin Hosptial, Department of Nephrology and Endocrinology Tokyo University, The Japanese Journal of Nephrology, The 29th Western/Eastern Regional Meeting, Japanese Society of Nephrology, vol. 41, No. 6 (517-684), Sep. 25, 1999, p. 614.

Hiroyuki Takeya et al., "Synergistic effect of sphingosine 1-phosphate on thrombin-induced tissue factor expression in endothelial cells", Blood published by the American Society of Hematology, vol. 102, No. 5, Sep. 1, 2003, pp. 1693-1700.

Yasuhiro Gon et al., "$S1P_3$ receptor-induced reorganization of epithelial tight junctions compromises lung barrier integrity and is potentiated by TNF", Proceedings of the National Academy of Sciences of the United States of America, published by the National Academy of Sciences, vol. 102, No. 26, Jun. 28, 2005, pp. 9270-9275.

M. Forrest et al., "Immune Cell Regulation and Cardiovascular Effects of Sphingosine 1-Phosphate Receptor Agonists in Rodents are Mediated via Distinct Receptor Subtypes", The Journal of Pharmacology and Experimental Therapeutics, published by the American Society for Pharmacology and Experimental Therapeutics, vol. 309, No. 2, 2004, pp. 758-768.

Carl Buelow et al., "Die Umwandlung des Acetessigesters in Hydrazidin-Derivate", Berichte der Deutschen Chemischen Gesellschaft, published by Ferd. Dummler's Verlagsbuchhandlung, vol. 50, 1917, pp. 1478-1496.

Carl Bulow et al., "Conversion of ethyl acetoacetate into hydrazidine derivatives", Journal of the Chemical Society, Abstracts, vol. 114, No. I, XP-002596231, 1918, pp. 42-44.

Petra Frohberg, et al., "Lipoxygenase inhibitors. IV: Synthesis and cyclization reactions of open-chain N1-aryl-substituted amidrazones", Archivder Pharmazie, vol. 328, No. 6, XP-002596145, 1995, pp. 505-516.

Extneded European Search Report issued on Sep. 15, 2010, in European Patent Application No. 06811603.7.

Japanese Office Action issued May 15, 2012 in patent application No. 2007-539962 with partial English translation.

A. S. A. S. Shawali, et al., "Synthesis and Reactions of Phenylcarbamoylarylhydrazidic Chlorides", Tetrahedron, vol. 27, 1971, pp. 2517-2528.

M. K. A. Ibrahim, et al., "Reaction of Ethyl Chloroglyoxalate Arylhydrazone with Heterocyclic Amidine and Difunction Amino Derivatives", J. Indian Chem. Soc., vol. 65 (3), Mar. 1988, pp. 194-196 plus cover page.

Petra Frohberg, et al., "New Syntheses of Benzotriazepines by Non-Convenient Cyclization Reaction of $N^1$, $N^3$-Diarylamidrazones", Heterocycles, vol. 43, No. 12, 1996, pp. 2549-2552 plus cover page.

* cited by examiner

S1P₃ RECEPTOR ANTAGONIST

CROSS-REFERENCE TO RELATED APPLICATIONS

This application is a 371 of PCT/JP06/320296 filed Oct. 11, 2006 and claims the benefit of JP 2005-298111.

TECHNICAL FIELD

The present invention relates to a medicine, and more particularly to a novel arylamidrazone derivative having an antagonistic action against S1P$_3$ receptors and a medicine containing thereof as an active ingredient.

BACKGROUND ART

It has been known that S1P receptors whose ligand is sphingosine 1-phosphate (hereinafter, abbreviated to "S1P"), are G protein-coupled type receptors and play an important role in vivo. The receptors are currently classified into 5 subtypes (S1P$_1$, S1P$_2$, S1P$_3$, S1P$_4$ and S1P$_5$).

S1P$_3$ receptors are expressed in the vascular endothelial cells or vascular smooth muscle cells in the cardiovascular system, and are known to receive extracellular S1P stimuli and be coupled with Gi to activate MAPK (Mitogen-activated protein kinase) such as ERK (extracellular signal-regulated kinase) or with Gq/G12 to activate Rho (Ras homologue). Thus, it has been suggested that the S1P$_3$ receptors are associated with the progress of arteriosclerosis, intimal thickening, or vascular proliferative diseases such as solid tumors, diabetic retinopathy and the like. In fact, suramin which specifically inhibits S1P$_3$ receptors appears to be curatively effective for the disease model of arteriosclerosis. Thus, it is suggested that an S1P$_3$ receptor-specific antagonist is useful as a prophylactic or therapeutic agent for the disease (see Non-Patent Documents 1 to 8).

Furthermore, it has been observed that S1P$_3$ receptors are also expressed in human cardiac muscle cells. S1P$_3$ receptors induce the generation of inositol 3-phosphate (IP$_3$) through the action of Gq, while IP$_3$ in the cardiac muscle cells, which is induced by stimulating angiotensin II receptor, is believed to affect the development or progress of cardiac hypertrophy. Therefore, there is a possibility that S1P$_3$ receptors may also affect cardiac hypertrophy. Moreover, while the production of S1P is increased under the hypoxic stress caused by ischemia during acute myocardial infarction, it is suggested that ischemic reperfusion disorder might be caused by Ca$^{2+}$ overload involving S1P$_3$ receptors. Therefore, an antagonist of S1P$_3$ receptor is conceived to be useful as a prophylactic or therapeutic agent for cardiac hypertrophy or ischemic reperfusion disorder after acute myocardial infarction (see Non-Patent Documents 9 and 10).

Meanwhile, since the S1P$_3$ receptors are specifically expressed in the smooth muscle cells in the basilar artery of rats or human coronary vessels, the role of the S1P$_3$ receptors in these organs has been focused. In experiments using frontal basilar artery or coronary artery of dog, S1P exhibited dose-dependent vasoconstrictive effect through the action of Rho, suggesting that S1P may be a novel vasoconstrictor substance or spasm-inducing substance that acts through S1P$_3$ receptors. Actually, the vasconstrictive action of S1P in the frontal basilar artery of dog was inhibited by suramin or an S1P$_3$ receptor antisense. Therefore, it is indicated that S1P$_3$ receptor antagonist is useful as a prophylactic or therapeutic agent for cerebrovascular spasm after subarachnoid hemorrhage, angina pectoris or myocardial infarction caused by coronary spasm, or as a vasodilator (see Non-Patent Documents 10 to 14).

It is also suggested that S1P$_3$ receptors are possibly associated with the dose-dependent vasoconstrictive effect of sphingosylphosphorylcholine in the renal capillaries of rat or the proliferation of mesangial cells, and thus may play an important role on renal diseases such as glomerulonephritis. Therefore, an S1P$_3$ receptor antagonist is also suggested to be useful in preventing the progress of progressive renal disorder (see Non-Patent Documents 15 to 18).

However, although it is reported that S1P promotes the expression of tissue factor (TF) in the endothelial cells through the action of ERK, S1P together with thrombin also induces the expression of S1P$_3$ receptors, and thus it is suggested that S1P and S1P$_3$ receptors operate as a positive feedback mechanism for the promotion of TF expression. Therefore, it is suggested that S1P$_3$ receptors could also be involved in the thrombus formation in thrombosis (see Non-Patent Document 19).

Moreover, the relationship between the S1P$_3$ receptors and pulmonary diseases, atrial fibrillation or bradycardia has also been known. For example, while S1P is increasingly produced in the trachea due to inflammatory cytokines, S1P administered through the trachea in mice synergistically affects with TNF to cause pulmonary edema, which is caused by rapid opening of the tight junction through the function of the S1P$_3$ receptor, as indicated from an experiment using an S1P$_3$ receptor knockout mice. Therefore, it is suggested that S1P$_3$ receptor antagonist is useful as a prophylactic or therapeutic agent for pulmonary diseases caused by pulmonary edema (adult respiratory distress syndrome (ARDS) and the like) (see Non-Patent Document 20).

In another experiment using the S1P$_3$ receptor knockout mice, it has been also suggested that S1P possibly activates acetylcholine-sensitive K$^+$ current ($I_{K,ACh}$) through the action of S1P$_3$ receptors to cause a delay of sinoatrial node pacemaker, thereby resulting in bradycardia. Furthermore, the activation of $I_{K,ACh}$ leads to parasympathetic-mediated atrial fibrillation, and thus S1P$_3$ receptor antagonist is suggested to be useful as a prophylactic or therapeutic agent for bradycardia or parasympathetic-mediated atrial fibrillation (see Non-Patent Document 21).

As can be seen from the above, S1P$_3$ receptor antagonist is useful as a prophylactic or therapeutic agent for arteriosclerosis; intimal thickening; vascular proliferative diseases such as solid tumors, diabetic retinopathy and the like, cardiac failure; ischemic reperfusion disorder; cerebrovascular spasm after subarachnoid hemorrhage; angina pectoris or myocardial infarction caused by coronary spasm; progressive renal disorders such as glomerulonephritis; thrombosis; pulmonary diseases caused by pulmonary edema (ARDS and the like); bradycardia; parasympathetic-mediated atrial fibrillation and the like, or as a vasodilator.

Antagonist for S1P$_3$ receptors includes suramin or S1P$_3$ antisense as described above.

However, suramin has a molecular weight of more than 1200, and thus may exhibit poor oral absorption. Antisense has a problem in large-scale preparation, and the efficiency of introducing thereof is yet insufficient for pharmaceutical application. Phenylquinolinecarboxamide derivatives (see Patent Document 1) and aminophenylpropionic acid derivatives (see Patent Document 2) are disclosed as S1P$_3$ receptor antagonists of low molecular weight. Thiazolidine derivatives and thiazinane derivatives (see Patent Document 3), and arylamide derivatives (see Patent Document 12) are also disclosed as a compound having antagonistic function against S1P$_1$ and S1P$_3$ receptors. However, these compounds have not been used hitherto for clinical application. Other compounds exhibiting S1P receptor non-selective antagonistic action have been disclosed (see Patent Documents 4 to 7); however, the effect of these compounds on the S1P$_3$ receptors is not known. As discussed in the above, S1P$_3$ receptor-selective antagonist which is clinically applicable has been desired heretofore.

Meanwhile, as for examples of a compound having an arylamidrazone skeleton as the compound of the present invention does, Patent Document 8 discloses a compound represented by the following formula (A):

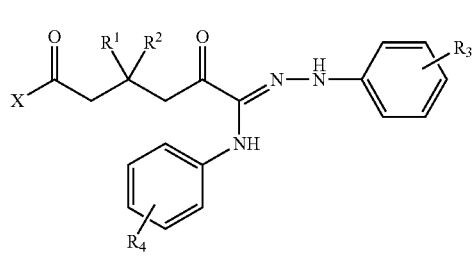

wherein R$_1$ and R$_2$, which are different, each represent a hydrogen atom, a methyl group or the like; R$_3$ represents a hydrogen atom, a halogen atom or the like; R$_4$ represents a hydrogen atom, a halogen atom, a nitro group or the like; and X represents an alkoxy group, an amino group or the like. Furthermore, Patent Document 9 discloses a compound represented by the following formula (B):

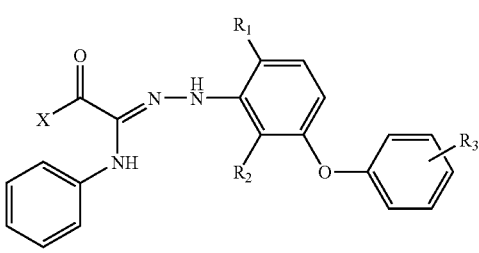

wherein R$_1$ represents a hydrogen atom, an alkyl group or the like; R$_2$ represents a hydrogen atom, a nitro group or the like; R$_3$ represents a hydrogen atom, a halogen atom or the like; and X represents a methyl group, an alkoxy group, an amino group or the like. Non-Patent Document 22 discloses a compound represented by the following formula (C):

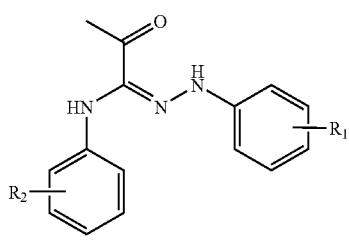

wherein R$_1$ represents a halogen atom, a methyl group or the like; and R$_2$ represents a hydrogen atom, a halogen atom or the like. However, none of the above-documents discloses the data indicating a specific antagonistic action against S1P$_3$ receptors as shown in the present application. Moreover, Non-Patent Document 23 discloses a compound represented by the following formula (D):

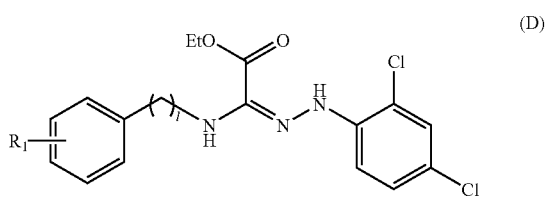

wherein l represents an integer of 0 or 1; when l is 0, R$_1$ represents a hydrogen atom, a 2-methyl group, a 4-methyl group, a 4-methoxy group or a 4-ethoxy group; and when l is 1, R$_1$ represents a hydrogen atom. However, this document only provides a method for synthesizing a hydrazidine derivative from ethyl acetoacetate, and the compound (D) is described only in the Preparative Example, without any description on what effect the compound would have on S1P$_3$ receptors.

Furthermore, Patent Documents 10 and 11 describe a compound having an arylamidrazone skeleton as an intermediate for obtaining a target substance, but the documents do not disclose any data suggesting a specific antagonistic action on the S1P$_3$ receptors as shown in the present application.

[Patent Document 1] JP-A-2002-332278
[Patent Document 2] JP-A-2005-247691
[Patent Document 3] WO 03/062392
[Patent Document 4] JP-A-2002-212070
[Patent Document 5] JP-A-2003-137894
[Patent Document 6] WO 03/040097
[Patent Document 7] WO 02/064616
[Patent Document 8] WO 92/19588
[Patent Document 9] JP-A-62-45568
[Patent Document 10] JP-A-54-3071
[Patent Document 11] DE 2724819 A
[Patent Document 12] WO 2006/063033
[Non-Patent Document 1] Cell, published by Cell Press, Vol. 99, p. 301-312 (1999)
[Non-Patent Document 2] Pharmacology & Therapeutics, published by Elsevier, USA, Vol. 88, p. 115-131 (2000)
[Non-Patent Document 3] Journal of Biological Chemistry, published by the American Society of Biochemistry and Molecular Biology, USA, vol. 276, p. 11830-11837 (2001)
[Non-Patent Document 4] American Journal of Respiratory Cell and Molecular Biology, published by the American Thoracic Society, USA, Vol. 46, p. 711-719 (2001)
[Non-Patent Document 5] Blood, published by the American Society of Hematology, USA, Vol. 102, p. 2099-2107 (2003)
[Non-Patent Document 6] Biochimica et Biophysica Acta, published by Elsevier, USA, Vol. 1582, p. 190-196 (2002)
[Non-Patent Document 7] Circulation, published by the American Heart Association, USA, Vol. 100, p. 861 (1999)
[Non-Patent Document 8] Cardiovascular Research, published by Elsevier, USA, Vol. 28, p. 1166 (1994)
[Non-Patent Document 9] European Journal of Biochemistry, published by Blackwell Publishing, Inc., UK, Vol. 267, p. 5679-5686 (2000)
[Non-Patent Document 10] The Journal of Histochemistry and Cytochemistry, published by the Histochemical Society, USA, Vol. 50, p. 661-670 (2002)

[Non-Patent Document 11] Circulation Research, published by the American Heart Association, USA, Vol. 91, p. 151-157 (2002)

[Non-Patent Document 12] Stroke, published by the American Heart Association, USA, Vol. 32, p. 2913-2919 (2001)

[Non-Patent Document 13] European Journal of Biochemistry, published by Blackwell Publishing, Inc., UK, Vol. 469, p. 125-134 (2003)

[Non-Patent Document 14] Arteriosclerosis, Thrombosis and Vascular Biology, published by the American Heart Association, USA, Vol. 24, p. 918-922 (2004)

[Non-Patent Document 15] Biochemical and Biophysical Research Communications, published by Elsevier, USA, Vol. 260, p. 203-208 (1999)

[Non-Patent Document 16] British Journal of Pharmacology, published by Nature Publishing Group, UK, Vol. 130, p. 1871-1877 (2000)

[Non-Patent Document 17] Genes Cells, published by Blackwell Publishing, Inc., UK, Vol. 7, p. 1217-1230 (2002)

[Non-Patent Document 18] The 29$^{th}$ Eastern Regional Meeting of the Japanese Society of Nephrology, Abstract, p. 614

[Non-Patent Document 19] Blood, published by the American Society of Hematology, USA, Vol. 102, p. 1693-1700 (2003)

[Non-Patent Document 20] Proceedings of the National Academy of Sciences of the United States of America, published by the National Academy of Sciences, USA, Vol. 102, p. 9270-9275 (2005)

[Non-Patent Document 21] The Journal of Pharmacology and Experimental Therapeutics, published by the American Society for Pharmacology and Experimental Therapeutics, USA, Vol. 309, p. 758-768 (2004)

[Non-Patent Document 22] Journal of Medicinal Chemistry, published by the American Chemical Society, USA, Vol. 45, p. 2123-2126 (2002)

[Non-Patent Document 23] Berichte der Deutschen Chemischen Gesellschaft, published by Ferd. Dummler's Verlagsbuchhandlung, Vol. 50, p. 1478-1496 (1917)

DISCLOSURE OF THE INVENTION

Problems to be Solved by the Invention

It is an object of the present invention to provide a low molecular weight compound which has an antagonistic action on S1P$_3$ receptors, and thus is useful as a pharmaceutical product.

Means for Solving the Problems

Under the above circumstances, the inventors of the present invention contemplated to develop an S1P$_3$ receptor antagonist as a pharmaceutical product, and earnestly conducted a search for low molecular weight compounds having an antagonistic action against S1P$_3$ receptors. The inventors have finally found that an arylamidrazone derivative represented by the following formula (1) or a pharmaceutically acceptable salt thereof has an excellent antagonistic action against S1P$_3$ receptors. Thus, the present invention is to provide an arylamidrazone derivative represented by the following formula (I):

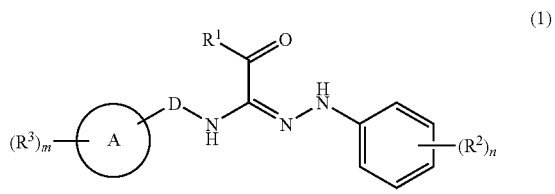

wherein $R^1$ represents a $C_2$-$C_8$ alkyl group which may be substituted, a phenyl group which may be substituted, an aromatic heterocyclic group which may be substituted, a $C_2$-$C_8$ alkoxy group which may be substituted, or —$NR^4R^5$ (wherein $R^4$ and $R^5$, which are identical or different, each represent a hydrogen atom or a lower alkyl group which may be substituted, or $R^4$ and $R^5$ may be joined with the adjacent nitrogen atom to form a nitrogen-containing heterocyclic ring which may be substituted);

$R^2$ and $R^3$, which are identical or different, each represent a hydrogen atom, a halogen atom, a halo-lower alkyl group, a lower alkyl group, a lower alkynyl group, a lower alkoxy group, a cyano group, a lower alkanoyl group or a lower alkylsulfonyl group;

A represents a benzene ring or a heterocyclic ring;

D represents a single bond or methylene;

m represents an integer from 1 to 3, and n represents an integer from 1 to 5 (with the proviso that the case where $R^1$ is an ethoxy group, $R^2$ is a 2,4-dichloro group, $R^3$ is a hydrogen atom, A is a benzene ring, and D is methylene; and the case where $R^1$ is an ethoxy group, $R^2$ is a 2,4-dichloro group, $R^3$ is a hydrogen atom, a 2-methyl group, a 4-methyl group, a 4-methoxy group or a 4-ethoxy group, A is a benzene ring, and D is a single bond, are excluded), or a pharmaceutical acceptable salt thereof.

Furthermore, the present invention is to provide a medicine containing the arylamidrazone derivative represented by the above formula (1) or a pharmaceutical acceptable salt thereof as an active ingredient.

The present invention is to provide a pharmaceutical composition containing the arylamidrazone derivative represented by the above formula (1) or the pharmaceutically acceptable salt thereof, and a pharmaceutically acceptable carrier.

The present invention is to provide a use of the arylamidrazone derivative represented by the above formula (1) or the pharmaceutically acceptable salt thereof for the manufacture of a medicine.

In addition, the present invention is to provide a method for treating arteriosclerosis, intimal thickening, solid tumors, diabetic retinopathy, cardiac failure, ischemic reperfusion disorder, cerebrovascular spasm after subarachnoid hemorrhage, angina pectoris or myocardial infarction caused by coronary spasm, glomerulonephritis, thrombosis, pulmonary diseases caused by pulmonary edema (ARDS), bradycardia, and parasympathetic-mediated atrial fibrillation, wherein the method comprising administering the arylamidrazone derivative represented by the above formula (1) or the pharmaceutically acceptable salt thereof.

Effects of The Invention

The arylamidrazone derivative represented by formula (1) of the present invention or a pharmaceutically acceptable salt thereof has an antagonistic action against S1P$_3$ receptors, and thus is useful as a prophylactic or therapeutic agent for various diseases caused by S1P$_3$ receptor stimulation, for example, arteriosclerosis, intimal thickening, vascular proliferative diseases (solid tumors, diabetic retinopathy and the like), cardiac failure, ischemic reperfusion disorder, cerebrovascular spasm after subarachnoid hemorrhage, angina pectoris or myocardial infarction caused by coronary spasm, progressive renal disorders such as glomerulonephritis, thrombosis, pulmonary diseases caused by pulmonary edema (ARDS and the like), bradycardia, parasympathetic-mediated atrial fibrillation or the like, or as a vasodilator.

BEST MODE FOR CARRYING OUT THE INVENTION

In the arylamidrazone derivative represented by formula (1), $R^1$ represents a $C_2$-$C_8$ alkyl group which may be substituted, a phenyl group which may be substituted, an aromatic heterocyclic group which may be substituted, a $C_2$-$C_8$ alkoxy group which may be substituted, or —$NR^4R^5$.

The $C_2$-$C_8$ alkyl group which may be substituted, which is represented by $R^1$, includes a straight-chained or branched alkyl group having 2 to 8 carbon atoms and a cyclic alkyl group having 3 to 7 carbon atoms, such as an ethyl group, an n-propyl group, an isopropyl group, a 1-ethylpropyl group, a 2,2-dimethylpropyl group, an n-butyl group, an isobutyl group, a sec-butyl group, a tert-butyl group, an n-pentyl group, a 2-propylpentyl group, an n-hexyl group, a cyclopentyl group, a cyclohexyl group and the like. Among them, a straight-chained or branched alkyl group having 2 to 6 carbon atoms is preferred, and a straight-chained or branched alkyl group having 2 to 4 carbon atoms is more preferred, with an n-butyl group, a tert-butyl group, a 11-ethylpropyl group and a 2,2-dimethylpropyl group being still more preferred.

Here, the group which may be substituted on the $C_2$-$C_8$ alkyl group includes a halogen atom, a lower alkoxy group and the like.

The phenyl group which may be substituted and the aromatic heterocyclic group which may be substituted, which are represented by $R^1$, include a phenyl group and an aromatic heterocyclic group unsubstituted or substituted by 1 to 3 substituents located at any arbitrary positions. Here, the aromatic heterocyclic group represents a 5- to 7-membered aromatic ring having one or two of oxygen, nitrogen, sulfur or other atoms, and specific examples include a furyl group, a thienyl group, a pyrrolyl group, a pyridyl group, a pyrimidyl group and the like, while a furyl group, a thienyl group and a pyridyl group are preferred. As the phenyl group which may be substituted or the aromatic heterocyclic group which may be substituted, a furyl group which may be substituted is still more preferred. Here, the group which may be substituted on the phenyl group or the aromatic heterocyclic group, includes a halogen atom, a lower alkyl group, a halo-lower alkyl group, a lower alkoxy group and the like. When two or more substituents are present, a combination of different groups may be used. Specific examples of a substituted phenyl group include a tolyl group, a trifluoromethylphenyl group, a methoxyphenyl group and the like, while specific examples of a substituted aromatic heterocyclic group, and particularly those of a substituted furyl group, include a chlorofuryl group (e.g., 5-chloro-2-furyl group), a bromofuryl group (e.g., a 3-bromo-2-furyl group), a methylfuryl group (e.g., 2-methyl-3-furyl group), an ethylfuryl group (e.g., 2-ethyl-3-furyl group), a methoxyfuryl group (e.g., 3-methoxy-2-furyl group), an ethoxyfuryl group (e.g., 3-ethoxy-2-furyl group) and the like.

The $C_2$-$C_8$ alkoxy group which may be substituted, which is represented by $R^1$, includes a straight-chained or branched alkoxy group having 2 to 8 carbon atoms, and a cyclic alkyloxy group having 3 to 6 carbon atoms, such as an ethoxy group, an n-propoxy group, an isopropoxy group, an n-butoxy group, an isobutoxy group, a sec-butoxy group, a tert-butoxy group, an n-pentyloxy group, a 2-propylpentyloxy group, an n-hexyloxy group, a cyclopentyloxy group, a cyclohexyloxy group and the like. Among them, an alkoxy group having 2 to 6 carbon atoms is preferred, and an alkoxy group having 2 to 4 carbon atoms is more preferred, with an ethoxy group being still more preferred. Here, the group which may be substituted on the $C_2$-$C_8$ alkoxy group includes a halogen atom, a lower alkoxy group and the like.

In addition, the halogen atom, lower alkyl group, halo-lower alkyl group or lower alkoxy group which may be substituted on the group represented by $R^1$, has the same meaning as the following respective groups represented by $R^2$ and $R^3$.

Substituents $R^2$ and $R^3$, which are identical or different, each represent a hydrogen atom, a halogen atom, a halo-lower alkyl group, a lower alkyl group, a lower alkynyl group, a lower alkoxy group, a cyano group, a lower alkanoyl group or a lower alkylsulfonyl group. The substitution positions for $R^2$ and $R^3$ are not particularly limited, but the meta-position or the para-position is preferred, while the para-position is more preferred. The number of substituents for $R^2$ (that is, n) is 1 to 5, and that for $R^3$ (that is, m) is 1 to 3, each of which is preferably 1 or 2.

The halogen atom represented by $R^2$ or $R^3$ includes fluorine, chlorine, bromine and iodine, and among them, fluorine, chlorine or bromine is preferred, with chlorine being more preferred.

The lower alkyl group represented by $R^2$ or $R^3$ includes an alkyl group having 1 to 8 carbon atoms ($C_1$-$C_8$ alkyl group). The $C_1$-$C_8$ alkyl group includes a straight-chained or branched alkyl group having 1 to 8 carbon atoms and a cyclic alkyl group having 3 to 7 carbon atoms, such as a methyl group, an ethyl group, an n-propyl group, an isopropyl group, an n-butyl group, an isobutyl group, a sec-butyl group, a tert-butyl group, an n-pentyl group, a 2-propylpentyl group, an n-hexyl group, a cyclopentyl group, a cyclohexyl group and the like. Among them, a straight-chained $C_1$-$C_8$ alkyl group is preferred, and a straight-chained alkyl group having 1 to 4 carbon atoms ($C_1$-$C_4$ alkyl group) is more preferred, with a methyl group being still more preferred.

The halo-lower alkyl group represented by $R^2$ or $R^3$ means the aforementioned lower alkyl group which is substituted with the aforementioned halogen atom, and may be specifically exemplified by a halo-$C_1$-$C_8$ alkyl group. Examples of the halo-lower alkyl group include a fluoromethyl group, a difluoromethyl group, a trifluoromethyl group, a chloromethyl group, a dichloromethyl group, a trichloromethyl group, a 2-chloro-1,1-dimethylethyl group and the like. Among them, a halo-$C_1$-$C_6$ alkyl group is preferred, and a halo-$C_1$-$C_4$ alkyl group is more preferred, with a trifluoromethyl group being still more preferred.

The lower alkynyl group represented by $R^2$ or $R^3$ includes a straight-chained, branched or cyclic hydrocarbon group having 2 to 6 carbon atoms and an unsaturated triple bond ($C_2$-$C_6$ alkynyl group), such as an ethynyl group, a 1-propynyl group, a 2-propynyl group, a 1-butynyl group, a 2-butynyl group, a 3-butynyl group, a 3-methyl-1-butynyl group, a 4-methyl-1-pentynyl group and the like. Among them, an alkynyl group having 2 to 4 carbon atoms ($C_2$-$C_4$ alkynyl group) is preferred, and an ethynyl group is more preferred.

The lower alkoxy group represented by $R^2$ or $R^3$ includes an alkoxy group having 1 to 8 carbon atoms ($C_1$-$C_8$ alkoxy group). The $C_1$-$C_8$ alkoxy group includes a straight-chained or branched alkoxy group having 1 to 8 carbon atoms and a cyclic alkyloxy group having 3 to 6 carbon atoms, such as a methoxy group, an ethoxy group, an n-propoxy group, an isopropoxy group, an n-butoxy group, an isobutoxy group, a sec-butoxy group, a tert-butoxy group, an n-pentyloxy group, a 2-propylpentyloxy group, an n-hexyloxy group, a cyclopentyloxy group, a cyclohexyloxy group and the like. Among them, an alkoxy group having 1 to 6 carbon atoms ($C_1$-$C_6$ alkoxy group) is preferred, and an alkoxy group having 1 to 4 carbon atoms ($C_1$-$C_4$ alkoxy group) is more preferred, with a methoxy group being still more preferred.

The lower alkanoyl group represented by $R_2$ or $R_3$ includes a straight-chained or branched alkanoyl group having 2 to 6 carbon atoms ($C_2$-$C_6$ alkanoyl group), such as an acetyl group, a propanoyl group, a butanoyl group and the like. Among them, an alkanoyl group having 2 to 4 carbon atoms ($C_2$-$C_4$ alkanoyl group) is preferred, and an acetyl group is more preferred.

The lower alkylsulfonyl group represented by $R^2$ or $R^3$ means a sulfonyl group substituted with the aforementioned lower alkyl group, and may be specifically exemplified by a $C_1$-$C_8$ alkylsulfonyl group. Examples of the lower alkylsulfonyl group include a methanesulfonyl group, an ethanesulfonyl group and the like. Among them, a $C_1$-$C_6$ alkylsulfonyl group is preferred, and a $C_1$-$C_4$ alkylsulfonyl group is more preferred, with a methanesulfonyl group being still more preferred.

$R^2$ and $R^3$ are each preferably a hydrogen atom, a halogen atom, a straight-chained $C_1$-$C_8$ alkyl group or a $C_2$-$C_6$ alkynyl group. The substitution position for $R^2$ and $R^3$ is preferably the meta-position or the para-position.

For the lower alkyl group represented by $R^4$ or $R^5$ which may be substituted, the lower alkyl group has the same meaning as that of the lower alkyl group represented by $R^2$ or $R^3$, and the lower alkyl group which may be substituted may have one to three substituents. Here, the group which may be substituted on the lower alkyl group includes the aforementioned halogen atom or lower alkoxy group.

$R^4$ and $R^5$ are each preferably a hydrogen atom or a tert-butyl group.

In the case where $R^4$ and $R^5$ are joined with the adjacent nitrogen atom to form a nitrogen-containing heterocyclic ring which may be substituted, the nitrogen-containing heterocyclic ring includes a 5- to 7-membered saturated heterocyclic ring or unsaturated heterocyclic ring, such as a pyrrole ring, a pyrrolidine ring, a pyrazole ring, a triazole ring, a piperazine ring, a piperidine ring and the like. Among them, a piperidine ring is preferred. The rings may also have one to four substituents located at any arbitrary positions. Here, the group which may be substituted on the nitrogen-containing heterocyclic ring includes the halogen atom, the lower alkyl group, the phenyl group, the lower alkoxy group or the like as previously mentioned.

A represents a benzene ring or a heterocyclic ring. The heterocyclic ring represented by A contains at least one or more of nitrogen, oxygen or sulfur atoms in the ring, and includes an alicyclic or aromatic heterocyclic ring which may be fused with an aromatic ring. Examples thereof include a pyrrole ring, a pyrazole ring, an imidazole ring, a pyridine ring, a pyrazine ring, a pyrimidine ring, an indole ring, a benzofuran ring, a quinoline ring, an isoquinoline ring, a benzothiazole ring, a benzoxazole ring and the like, and among them, a pyridine ring, a quinoline ring or an isoquinoline ring is preferred. A is preferably a benzene ring, a 2-pyridine ring, a 3-pyridine ring, a 4-pyridine ring, a 5-quinoline ring, an 8-quinoline ring, a 5-isoquinoline ring or an 8-isoquinoline ring, and is more preferably a benzene ring.

D represents a single bond or methylene, but is more preferably a single bond.

When D is a single bond, the compound of formula (1) is represented by the following formula (1a):

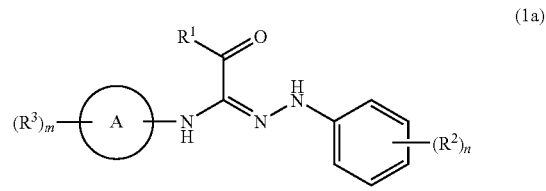

(1a)

wherein $R^1$ represents a $C_2$-$C_8$ alkyl group which may be substituted, a phenyl group which may be substituted, an aromatic heterocyclic group which may be substituted, a $C_2$-$C_8$ alkoxy group which may be substituted, or —$NR^4R^5$ (wherein $R^4$ and $R^5$, which are identical or different, each represent a hydrogen atom or a lower alkyl group which may be substituted, or $R^4$ and $R^5$ may be joined with the adjacent nitrogen atom to form a nitrogen-containing heterocyclic ring which may be substituted);

$R^2$ and $R^3$, which are identical or different, each represent a hydrogen atom, a halogen atom, a halo-lower alkyl group, a lower alkyl group, a lower alkynyl group, a lower alkoxy group, a cyano group, a lower alkanoyl group or a lower alkylsulfonyl group;

A represents a benzene ring or a heterocyclic ring;

m represents an integer from 1 to 3, and n represents an integer from 1 to 5 (with the proviso that the case where $R^1$ is an ethoxy group, $R^2$ is a 2,4-dichloro group, $R^3$ is a hydrogen atom, a 2-methyl group, a 4-methyl group, a 4-methoxy group or a 4-ethoxy group, and A is a benzene ring, is excluded).

Among the compounds (1) of the present invention, the each substituent in the formula (1) are preferably the following, from the viewpoint of high selectivity to the $S1P_3$ receptors. Specifically, $R^1$ is preferably a $C_2$-$C_8$ straight-chained or branched alkyl group which may be substituted with a halogen atom or a $C_1$-$C_8$ alkyl group, or a furyl group which may be substituted with a halogen atom, a $C_1$-$C_8$ alkyl group, a halo-$C_1$-$C_8$ alkyl group or a $C_1$-$C_8$ alkoxy group, and more preferably a straight-chained or branched $C_2$-$C_8$ alkyl group. $R^2$ and $R^3$ are each preferably a hydrogen atom, a halogen atom, a straight-chained $C_1$-$C_8$ alkyl group or a $C_2$-$C_6$ alkynyl group. The substitution position for $R^2$ and $R^3$ are preferably the meta-position or the para-position. m and n are each preferably 1 or 2. Furthermore, A is preferably a benzene ring, and D is preferably a single bond.

The present invention also includes pharmaceutically acceptable salts of the compound of formula (1). Specific examples of the salts include salts with inorganic acids such as hydrochloride, hydrobromide, hydroiodide, sulfate, nitrate and phosphate; salts with organic acids such as acetate, trifluoroacetate, oxalate, fumarate, maleate, tartrate, mesylate and tosylate; and the like. The salts of the compound of formula (1) can be obtained according to standard methods.

The compound (1) of the present invention also includes hydrates and various solvates. The compound of the present invention further includes all crystal forms thereof.

Specific examples of the compound (1) of the present invention include:
2-(4-chlorophenylhydrazono)-2-(3-fluorophenylamino)acetophenone,
2-(4-chlorophenylhydrazono)-2-(3-trifluoromethylphenylamino)acetophenone,
2-(4-chlorophenylhydrazono)-2-(2,3-difluorophenylamino)acetophenone, 2-(4-chlorophenylhydrazono)-2-(2,6-dichloropyridin-4-ylamino)acetophenone,
2-(4-chlorophenylhydrazono)-2-[(4-fluorophenyl)methylamino]acetophenone,
2-(4-chlorophenylhydrazono)-2-[(2,5-difluorophenyl)methylamino]acetophenone,
2-(4-chlorophenylhydrazono)-2-[(3-trifluoromethylphenyl)methylamino]acetophenone,
2-(4-chlorophenylhydrazono)-2-(2-fluorophenylamino)acetophenone,
2-(4-chlorophenylhydrazono)-2-(4-fluorophenylamino)acetophenone,
2-(2-chlorophenylamino)-2-(4-chlorophenylhydrazono)acetophenone,
2-(3-chlorophenylamino)-2-(4-chlorophenylhydrazono)acetophenone,
2-(4-chlorophenylamino)-2-(4-chlorophenylhydrazono)acetophenone,
ethyl 1-(4-chlorophenylhydrazono)-1-(3-fluorophenylamino)acetate,
ethyl 1-(4-chlorophenylamino)-1-(4-chlorophenylhydrazono)acetate,
ethyl 1-(4-chlorophenylhydrazono)-1-[(2,5-difluorophenyl)methylamino]acetate,
ethyl 1-(4-chlorophenylhydrazono)-1-(3-trifluoromethylphenylamino)acetate,
ethyl 1-(4-chlorophenylhydrazono)-1-(3,5-difluorophenylamino)acetate,
ethyl 1-(4-chlorophenylhydrazono)-1-(3,5-dichlorophenylamino)acetate,
ethyl 1-(4-chlorophenylhydrazono)-1-(phenylamino)acetate,
ethyl 1-(4-chlorophenylhydrazono)-1-(3-cyanophenylamino)acetate,
[1-(4-chlorophenylhydrazono)-1-(3-fluorophenylamino)acetyl]piperidine,
[1-(4-chlorophenylhydrazono)-1-(3,5-dichlorophenylamino)acetyl]piperidine,
[1-(4-chlorophenylamino)-1-(4-chlorophenylhydrazono)acetyl]piperidine,
[1-(3-chlorophenylamino)-1-(4-chlorophenylhydrazono)acetyl]piperidine,
[1-(4-chlorophenylhydrazono)-1-(3,5-difluorophenylamino)acetyl]piperidine,
[1-(4-chlorophenylhydrazono)-1-(3,4-dichlorophenylamino)acetyl]piperidine,
[1-(4-chlorophenylhydrazono)-1-(3-cyanophenylamino)acetyl]piperidine,
N-tert-butyl-[1-(4-chlorophenylhydrazono)-1-(3-fluoro phenylamino)]acetamide,
N-tert-butyl-[1-(4-chlorophenylamino)-1-(4-chlorophenylhydrazono)]acetamide,
N-tert-butyl-[1-(4-chlorophenylhydrazono)-1-(3,5-dichlorophenylamino)]acetamide,
N-tert-butyl-[1-(4-chlorophenylhydrazono)-1-(3,4-dichlorophenylamino)]acetamide,
1-(4-chlorophenylhydrazono)-1-(3-fluorophenylamino)-3,3-dimethyl-2-butanone,
1-(4-chlorophenylamino)-1-(4-chlorophenylhydrazono)-3,3-dimethyl-2-butanone,
1-(4-chlorophenylhydrazono)-1-(3,5-difluorophenylamino)-3,3-dimethyl-2-butanone,
1-(4-chlorophenylhydrazono)-1-(2,6-dichloropyridin-4-ylamino)-3,3-dimethyl-2-butanone,
1-(4-chlorophenylhydrazono)-1-(3-trifluoromethylphenylamino)-3,3-dimethyl-2-butanone,
1-(4-chlorophenylhydrazono)-1-(3,5-dichlorophenylamino)-3,3-dimethyl-2-butanone,
1-(4-chlorophenylhydrazono)-1-(3,4-dichlorophenylamino)-3,3-dimethyl-2-butanone,
1-(4-chlorophenylhydrazono)-1-[(3,5-dichlorophenyl)methylamino]-3,3-dimethyl-2-butanone,
1-(4-chlorophenylhydrazono)-1-(2,4-dichlorophenylamino)-3,3-dimethyl-2-butanone,
1-(3-chlorophenylhydrazono)-1-(3-fluorophenylamino)-3,3-dimethyl-2-butanone,
1-(4-chlorophenylamino)-1-(3-chlorophenylhydrazono)-3,3-dimethyl-2-butanone,
1-(3-chlorophenylhydrazono)-1-(3,5-dichlorophenylamino)-3,3-dimethyl-2-butanone,
1-(3-chlorophenylhydrazono)-1-(3,4-dichlorophenylamino)-3,3-dimethyl-2-butanone,
1-(2-chlorophenylhydrazono)-1-(3-fluorophenylamino)-3,3-dimethyl-2-butanone,
1-(4-chlorophenylamino)-1-(2-chlorophenylhydrazono)-3,3-dimethyl-2-butanone,
1-(2-chlorophenylhydrazono)-1-(3,5-dichlorophenylamino)-3,3-dimethyl-2-butanone,
1-(2-chlorophenylhydrazono)-1-(3,4-dichlorophenylamino)-3,3-dimethyl-2-butanone,
1-(3-fluorophenylamino)-1-(phenylhydrazono)-3,3-dimethyl-2-butanone,
1-(4-chlorophenylamino)-1-(phenylhydrazono)-3,3-dimethyl-2-butanone,
1-(3,5-dichlorophenylamino)-1-(phenylhydrazono)-3,3-dimethyl-2-butanone,
1-(3,4-dichlorophenylamino)-1-(phenylhydrazono)-3,3-dimethyl-2-butanone,
1-(3-fluorophenylamino)-1-(4-fluorophenylhydrazono)-3,3-dimethyl-2-butanone,
1-(4-fluorophenylamino)-1-(4-fluorophenylhydrazono)-3,3-dimethyl-2-butanone,
1-(4-chlorophenylamino)-1-(4-fluorophenylhydrazono)-3,3-dimethyl-2-butanone,
1-(4-bromophenylamino)-1-(4-fluorophenylhydrazono)-3,3-dimethyl-2-butanone,
1-(4-fluorophenylhydrazono)-1-(4-methoxyphenylamino)-3,3-dimethyl-2-butanone,
1-(4-fluorophenylhydrazono)-1-(4-trifluoromethylphenylamino)-3,3-dimethyl-2-butanone,
1-(3,5-dichlorophenylamino)-1-(4-fluorophenylhydrazono)-3,3-dimethyl-2-butanone,
1-(3,4-dichlorophenylamino)-1-(4-fluorophenylhydrazono)-3,3-dimethyl-2-butanone,
1-(3-fluorophenylamino)-1-(4-methylphenylhydrazono)-3,3-dimethyl-2-butanone,
1-(4-chlorophenylamino)-1-(4-methylphenylhydrazono)-3,3-dimethyl-2-butanone,
1-(4-methylphenylamino)-1-(4-methylphenylhydrazono)-3,3-dimethyl-2-butanone,
1-(3,5-dichlorophenylamino)-1-(4-methylphenylhydrazono)-3,3-dimethyl-2-butanone,
1-(3,4-dichlorophenylamino)-1-(4-methylphenylhydrazono)-3,3-dimethyl-2-butanone,
1-(3-fluorophenylamino)-1-(4-trifluoromethylphenylhydrazono)-3,3-dimethyl-2-butanone,
1-(4-fluorophenylamino)-1-(4-trifluoromethylphenylhydrazono)-3,3-dimethyl-2-butanone,
1-(4-chlorophenylamino)-1-(4-trifluoromethylphenylhydrazono)-3,3-dimethyl-2-butanone,
1-(4-bromophenylamino)-1-(4-trifluoromethylphenylhydrazono)-3,3-dimethyl-2-butanone, 1-(4-trifluoromethylphenylamino)-1-(4-trifluoromethylphenylhydrazono)-3,3-dimethyl-2-butanone,
1-(3,5-dichlorophenylamino)-1-(4-trifluoromethylphenylhydrazono)-3,3-dimethyl-2-butanone,
1-(3,4-dichlorophenylamino)-1-(4-trifluoromethylphenylhydrazono)-3,3-dimethyl-2-butanone,
1-(4-bromophenylhydrazono)-1-(3-fluorophenylamino)-3,3-dimethyl-2-butanone,
1-(4-bromophenylhydrazono)-1-(4-fluorophenylamino)-3,3-dimethyl-2-butanone,
1-(4-bromophenylhydrazono)-1-(4-chlorophenylamino)-3,3-dimethyl-2-butanone,
1-(4-bromophenylamino)-1-(4-bromophenylhydrazono)-3,3-dimethyl-2-butanone,
1-(4-bromophenylhydrazono)-1-(4-cyanophenylamino)-3,3-dimethyl-2-butanone,
1-(4-bromophenylhydrazono)-1-(4-ethynylphenylamino)-3,3-dimethyl-2-butanone,
1-(4-bromophenylhydrazono)-1-(3,5-dichlorophenylamino)-3,3-dimethyl-2-butanone,
1-(4-bromophenylhydrazono)-1-(3,4-dichlorophenylamino)-3,3-dimethyl-2-butanone,
1-(4-cyanophenylhydrazono)-1-(3-fluorophenylamino)-3,3-dimethyl-2-butanone,
1-(4-cyanophenylhydrazono)-1-(4-fluorophenylamino)-3,3-dimethyl-2-butanone,
1-(4-chlorophenylamino)-1-(4-cyanophenylhydrazono)-3,3-dimethyl-2-butanone,
1-(4-bromophenylamino)-1-(4-cyanophenylhydrazono)-3,3-dimethyl-2-butanone,
1-(4-cyanophenylamino)-1-(4-cyanophenylhydrazono)-3,3-dimethyl-2-butanone,
1-(4-cyanophenylhydrazono)-1-(4-ethynylphenylamino)-3,3-dimethyl-2-butanone,
1-(4-cyanophenylhydrazono)-1-(4-methoxyphenylamino)-3,3-dimethyl-2-butanone,
1-(4-cyanophenylhydrazono)-1-(3,5-dichlorophenylamino)-3,3-dimethyl-2-butanone,
1-(4-cyanophenylhydrazono)-1-(3,4-dichlorophenylamino)-3,3-dimethyl-2-butanone,
1-(4-chlorophenylamino)-1-(4-methoxyphenylhydrazono)-3,3-dimethyl-2-butanone,
1-(4-acetylphenylhydrazono)-1-(3-fluorophenylamino)-3,3-dimethyl-2-butanone,
1-(4-acetylphenylhydrazono)-1-(4-fluorophenylamino)-3,3-dimethyl-2-butanone,
1-(4-acetylphenylhydrazono)-1-(4-chlorophenylamino)-3,3-dimethyl-2-butanone,
1-(4-acetylphenylhydrazono)-1-(4-bromophenylamino)-3,3-dimethyl-2-butanone,
1-(4-acetylphenylhydrazono)-1-(4-ethynylphenylamino)-3,3-dimethyl-2-butanone,
1-(4-acetylphenylhydrazono)-1-(4-methoxyphenylamino)-3,3-dimethyl-2-butanone,
1-(3-fluorophenylamino)-1-(4-methanesulfonylphenylhydrazono)-3,3-dimethyl-2-butanone,
1-(4-fluorophenylamino)-1-(4-methanesulfonylphenylhydrazono)-3,3-dimethyl-2-butanone,
1-(4-chlorophenylamino)-1-(4-methanesulfonylphenylhydrazono)-3,3-dimethyl-2-butanone,
1-(4-bromophenylamino)-1-(4-methanesulfonylphenylhydrazono)-3,3-dimethyl-2-butanone,
1-(4-ethynylphenylamino)-1-(4-methanesulfonylphenylhydrazono)-3,3-dimethyl-2-butanone,
1-(4-acetylphenylamino)-1-(4-methanesulfonylphenylhydrazono)-3,3-dimethyl-2-butanone,
1-(4-isopropylphenylamino)-1-(4-methanesulfonylphenylhydrazono)-3,3-dimethyl-2-butanone,
1-(3,4-dichlorophenylhydrazono)-1-(3-fluorophenylamino)-3,3-dimethyl-2-butanone,
1-(4-bromophenylhydrazono)-1-(4-chloro-3-fluorophenylamino)-3,3-dimethyl-2-butanone,
1-(4-chlorophenylamino)-1-(4-ethynylphenylhydrazono)-3,3-dimethyl-2-butanone,
1-(3,4-dichlorophenylhydrazono)-1-(3-ethynylphenylamino)-3,3-dimethyl-2-butanone,
1-(3-chlorophenylamino)-1-(4-ethynylphenylhydrazono)-3,3-dimethyl-2-butanone,
1-(4-chlorophenylhydrazono)-1-(3,4-dichlorophenylamino)-2-hexanone,
1-(4-chlorophenylamino)-1-(4-chlorophenylhydrazono)-3-ethyl-2-pentanone,
1-(4-chlorophenylhydrazono)-1-(4-ethynylphenylamino)-2-hexanone,
1-(4-chlorophenylhydrazono)-1-(4-fluorophenylamino)-3-ethyl-2-pentanone,
1-(4-chlorophenylhydrazono)-1-(3-fluorophenylamino)-4,4-dimethyl-2-pentanone,
1-(4-chlorophenylhydrazono)-1-(4-fluorophenylamino)-4,4-dimethyl-2-pentanone,
1-(4-chlorophenylamino)-1-(4-chlorophenylhydrazono)-2-hexanone,
1-(4-chlorophenylamino)-1-(4-chlorophenylhydrazono)-2-(2-furyl)-2-ethanone,
1-(4-chlorophenylhydrazono)-1-(4-ethynylphenylamino)-2-(2-furyl)-2-ethanone,
1-(4-chlorophenylhydrazono)-1-(4-fluorophenylamino)-2-(2-furyl)-2-ethanone,
1-(4-bromophenylamino)-1-(4-chlorophenylhydrazono)-2-(2-furyl)-2-ethanone,
1-(4-chlorophenylhydrazono)-1-(3-trifluoromethylphenylamino)-2-(2-furyl)-2-ethanone,
4-chloro-1-(4-chlorophenylhydrazono)-1-(3-trifluoromethylphenylamino)-3,3-dimethyl-2-butanone,
4-chloro-1-(4-chlorophenylhydrazono)-1-(4-ethynylphenylamino)-3,3-dimethyl-2-butanone,
1-(3-chlorophenylamino)-1-(3,4-dichlorophenylhydrazono)-3,3-dimethyl-2-butanone,
1-(4-chlorophenylamino)-1-(3,4-dichlorophenylhydrazono)-3,3-dimethyl-2-butanone,
1-(4-chlorophenylamino)-1-(4-chlorophenylhydrazono)-2-(2-thienyl)-2-ethanone,
1-(4-chlorophenylhydrazono)-1-(isoquinolin-5-ylamino)-3,3-dimethyl-2-butanone,
1-(4-chlorophenylhydrazono)-1-(quinolin-8-ylamino)-3,3-dimethyl-2-butanone,
1-(4-chlorophenylhydrazono)-1-(pyridin-3-ylamino)-3,3-dimethyl-2-butanone,
1-(4-chlorophenylhydrazono)-1-(5-chloropyridin-2-ylamino)-3,3-dimethyl-2-butanone,
1-(4-chlorophenylamino)-1-(4-chlorophenylhydrazono)-2-(4-trifluoromethylphenyl)-2-ethanone,
1-(3-fluorophenylamino)-1-(4-ethynylphenylhydrazono)-3,3-dimethyl-2-butanone,
1-(3,4-dichlorophenylhydrazono)-1-(4-ethynylphenylamino)-3,3-dimethyl-2-butanone,
1-(3-chlorophenylamino)-1-(4-chlorophenylhydrazono)-3,3-dimethyl-2-butanone,
1-(3-bromophenylamino)-1-(4-chlorophenylhydrazono)-3,3-dimethyl-2-butanone,
1-(4-chloro-3-fluorophenylamino)-1-(4-chlorophenylhydrazono)-3,3-dimethyl-2-butanone, 1-(4-chlorophenylhydrazono)-1-(4-ethynylphenylamino)-3,3-dimethyl-2-butanone,
1-(3-chlorophenylamino)-1-(4-chlorophenylhydrazono)-3-ethyl-2-pentanone,
1-(4-ethynylphenylamino)-1-(4-ethynylphenylhydrazono)-3,3-dimethyl-2-butanone,
1-(4-chlorophenylamino)-1-(4-chlorophenylhydrazono)-4,4-dimethyl-2-pentanone,
1-(3-chlorophenylamino)-1-(4-chlorophenylhydrazono)-4,4-dimethyl-2-pentanone,
1-(3-chlorophenylamino)-1-(4-chlorophenylhydrazono)-2-hexanone, and pharmaceutically acceptable salts thereof. Among them, preferred is:
1-(4-chlorophenylhydrazono)-1-(3-fluorophenylamino)-3,3-dimethyl-2-butanone,
1-(4-chlorophenylamino)-1-(4-chlorophenylhydrazono)-3,3-dimethyl-2-butanone,
1-(4-chlorophenylhydrazono)-1-(3,5-difluorophenylamino)-3,3-dimethyl-2-butanone,
1-(4-chlorophenylhydrazono)-1-(3,5-dichlorophenylamino)-3,3-dimethyl-2-butanone,
1-(4-chlorophenylhydrazono)-1-(3,4-dichlorophenylamino)-3,3-dimethyl-2-butanone,
1-(3-chlorophenylhydrazono)-1-(3-fluorophenylamino)-3,3-dimethyl-2-butanone,
1-(4-chlorophenylamino)-1-(3-chlorophenylhydrazono)-3,3-dimethyl-2-butanone,
1-(3-chlorophenylhydrazono)-1-(3,5-dichlorophenylamino)-3,3-dimethyl-2-butanone,
1-(3-chlorophenylhydrazono)-1-(3,4-dichlorophenylamino)-3,3-dimethyl-2-butanone,
1-(3-fluorophenylamino)-1-(phenylhydrazono)-3,3-dimethyl-2-butanone,
1-(4-chlorophenylamino)-1-(phenylhydrazono)-3,3-dimethyl-2-butanone,
1-(3,5-dichlorophenylamino)-1-(phenylhydrazono)-3,3-dimethyl-2-butanone,
1-(3,4-dichlorophenylamino)-1-(phenylhydrazono)-3,3-dimethyl-2-butanone,
1-(3-fluorophenylamino)-1-(4-fluorophenylhydrazono)-3,3-dimethyl-2-butanone,
1-(4-fluorophenylamino)-1-(4-fluorophenylhydrazono)-3,3-dimethyl-2-butanone,
1-(4-chlorophenylamino)-1-(4-fluorophenylhydrazono)-3,3-dimethyl-2-butanone,
1-(4-bromophenylamino)-1-(4-fluorophenylhydrazono)-3,3-dimethyl-2-butanone,
1-(3,5-dichlorophenylamino)-1-(4-fluorophenylhydrazono)-3,3-dimethyl-2-butanone,
1-(3,4-dichlorophenylamino)-1-(4-fluorophenylhydrazono)-3,3-dimethyl-2-butanone,
1-(3-fluorophenylamino)-1-(4-methylphenylhydrazono)-3,3-dimethyl-2-butanone,
1-(4-chlorophenylamino)-1-(4-methylphenylhydrazono)-3,3-dimethyl-2-butanone,
1-(4-methylphenylamino)-1-(4-methylphenylhydrazono)-3,3-dimethyl-2-butanone,
1-(3,5-dichlorophenylamino)-1-(4-methylphenylhydrazono)-3,3-dimethyl-2-butanone,
1-(3,4-dichlorophenylamino)-1-(4-methylphenylhydrazono)-3,3-dimethyl-2-butanone,
1-(4-bromophenylhydrazono)-1-(3-fluorophenylamino)-3,3-dimethyl-2-butanone,
1-(4-bromophenylhydrazono)-1-(4-fluorophenylamino)-3,3-dimethyl-2-butanone,
1-(4-bromophenylhydrazono)-1-(4-chlorophenylamino)-3,3-dimethyl-2-butanone,
1-(4-bromophenylamino)-1-(4-bromophenylhydrazono)-3,3-dimethyl-2-butanone,
1-(4-bromophenylhydrazono)-1-(4-ethynylphenylamino)-3,3-dimethyl-2-butanone,
1-(4-bromophenylhydrazono)-1-(3,5-dichlorophenylamino)-3,3-dimethyl-2-butanone,
1-(4-bromophenylhydrazono)-1-(3,4-dichlorophenylamino)-3,3-dimethyl-2-butanone,
1-(3,4-dichlorophenylhydrazono)-1-(3-fluorophenylamino)-3,3-dimethyl-2-butanone,
1-(4-bromophenylhydrazono)-1-(4-chloro-3-fluorophenylamino)-3,3-dimethyl-2-butanone,
1-(4-chlorophenylamino)-1-(4-ethynylphenylhydrazono)-3,3-dimethyl-2-butanone,
1-(3,4-dichlorophenylhydrazono)-1-(3-ethynylphenylamino)-3,3-dimethyl-2-butanone,
1-(3-chlorophenylamino)-1-(4-ethynylphenylhydrazono)-3,3-dimethyl-2-butanone,
1-(4-chlorophenylhydrazono)-1-(3,4-dichlorophenylamino)-2-hexanone,
1-(4-chlorophenylamino)-1-(4-chlorophenylhydrazono)-3-ethyl-2-pentanone,
1-(4-chlorophenylhydrazono)-1-(4-ethynylphenylamino)-2-hexanone,
1-(4-chlorophenylhydrazono)-1-(4-fluorophenylamino)-3-ethyl-2-pentanone,
1-(4-chlorophenylhydrazono)-1-(3-fluorophenylamino)-4,4-dimethyl-2-pentanone,
1-(4-chlorophenylhydrazono)-1-(4-fluorophenylamino)-4,4-dimethyl-2-pentanone,
1-(4-chlorophenylamino)-1-(4-chlorophenylhydrazono)-2-hexanone,
1-(4-chlorophenylamino)-1-(4-chlorophenylhydrazono)-2-(2-furyl)-2-ethanone,
1-(4-chlorophenylhydrazono)-1-(4-ethynylphenylamino)-2-(2-furyl)-2-ethanone,
1-(4-chlorophenylhydrazono)-1-(4-fluorophenylamino)-2-(2-furyl)-2-ethanone,
1-(4-bromophenylamino)-1-(4-chlorophenylhydrazono)-2-(2-furyl)-2-ethanone,
4-chloro-1-(4-chlorophenylhydrazono)-1-(4-ethynylphenylamino)-3,3-dimethyl-2-butanone,
1-(3-chlorophenylamino)-1-(3,4-dichlorophenylhydrazono)-3,3-dimethyl-2-butanone,
1-(4-chlorophenylamino)-1-(3,4-dichlorophenylhydrazono)-3,3-dimethyl-2-butanone,
1-(3-fluorophenylamino)-1-(4-ethynylphenylhydrazono)-3,3-dimethyl-2-butanone,
1-(3,4-dichlorophenylhydrazono)-1-(4-ethynylphenylamino)-3,3-dimethyl-2-butanone,
1-(3-chlorophenylamino)-1-(4-chlorophenylhydrazono)-3,3-dimethyl-2-butanone,
1-(4-bromophenylamino)-1-(4-chlorophenylhydrazono)-3,3-dimethyl-2-butanone,
1-(4-chloro-3-fluorophenylamino)-1-(4-chlorophenylhydrazono)-3,3-dimethyl-2-butanone,
1-(4-chlorophenylhydrazono)-1-(4-ethynylphenylamino)-3,3-dimethyl-2-butanone,
1-(3-chlorophenylamino)-1-(4-chlorophenylhydrazono)-3-ethyl-2-pentanone,
1-(4-ethynylphenylamino)-1-(4-ethynylphenylhydrazono)-3,3-dimethyl-2-butanone,
1-(4-chlorophenylamino)-1-(4-chlorophenylhydrazono)-4,4-dimethyl-2-pentanone,
1-(3-chlorophenylamino)-1-(4-chlorophenylhydrazono)-4,4-dimethyl-2-pentanone, 1-(3-chlorophenylamino)-1-(4-chlorophenylhydrazono)-2-hexanone, and pharmaceutically acceptable salts thereof.

As the method for producing the arylamidrazone derivative represented by formula (1) of the present invention includes the following method, but the method for producing the compound of the present invention is not limited thereto.

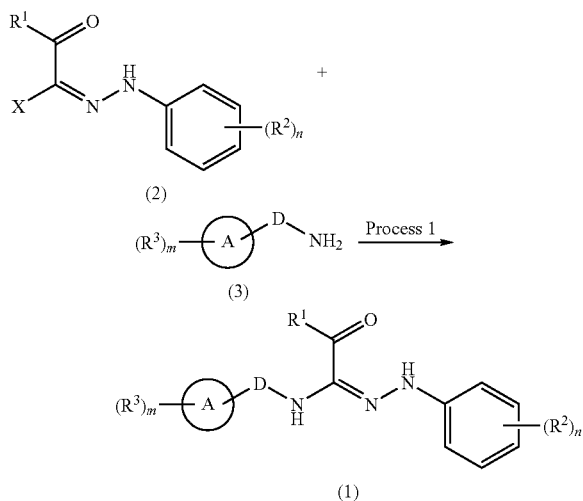

wherein $R^1$, $R^2$, $R^3$, A, D, m and n have the same meanings as defined above, and X represents a halogen atom.

[Process 1]

The arylamidrazone derivative (1) of the present invention is obtained by reacting a compound (2) with a compound (3). The reaction between the compound (2) and the compound (3) is performed by reacting them in the presence of an organic base (for example, triethylamine, pyridine or the like), in a solvent such as ether (for example, diethyl ether, tetrahydrofuran or the like), alcohol (methanol, ethanol or the like) or a mixture thereof, at a reaction temperature of 0 to 60° C. for 1 to 24 hours.

A method for producing the compound (2) which is an intermediate for the synthesis of the compound of the present invention will hereinafter be described.

[Process 2]

A compound (6) is obtained by reacting a diazonium salt derivative represented by compound (4) with a compound (5) according to the method as described in the literature (J. Med. Chem. 45, 2123 (2002)).

The reaction between the diazonium salt derivative (4) and the compound (5) is performed by reacting them in the presence of a base (for example, a carboxylic acid salt of alkali metal such as sodium acetate, an aromatic base such as pyridine, or the like), in a solvent mixture of water with alcohol (for example, methanol, ethanol or the like) and/or ether (for example, diethyl ether, tetrahydrofuran or the like), at a reaction temperature of 0 to 40° C. for 1 to 24 hours. The diazonium salt derivative (4) can be obtained by adding dropwise a solution of a nitrous acid salt such as sodium nitrite to a hydrochloric acid solution of a corresponding aniline derivative.

[Process 3]

Subsequently, the compound (2) can be obtained by reacting the compound (6) with a halogen acetic acid solution in the presence of a base (for example, a carboxylic acid salt of alkali metal such as sodium acetate), in a solvent mixture of acetic acid/acetic anhydride, at a reaction temperature of 0 to 40° C. for 1 to 24 hours.

[Process 4]

The compound (2) can also be obtained according to the following method. The compound (2) can be obtained by reacting a diazonium salt derivative (4) with a compound (7) in the presence of a base (for example, a carboxylic acid salt of alkali metal such as sodium acetate, an aromatic base such as pyridine, or the like), in a solvent mixture of water and an alcohol (for example, methanol, ethanol or the like), at a temperature of 0 to 40° C. for 1 to 24 hours.

The compound (7) can be synthesized according to the method described in the literature (J. Org. Chem. 43, 3821 (1978)) when $R^1$ is an amino group, or according to the method described in the literatures (J. Am. Chem. Soc. 66, 1222 (1944), Tetrahedron Lett. 46, 623 (2005), and U.S. Pat. No. 4,053,594) when $R^1$ is a lower alkyl group such as a t-butyl group.

The compound of formula (1) produced as such can be isolated and purified by conventional method such as recrystallization or column chromatography.

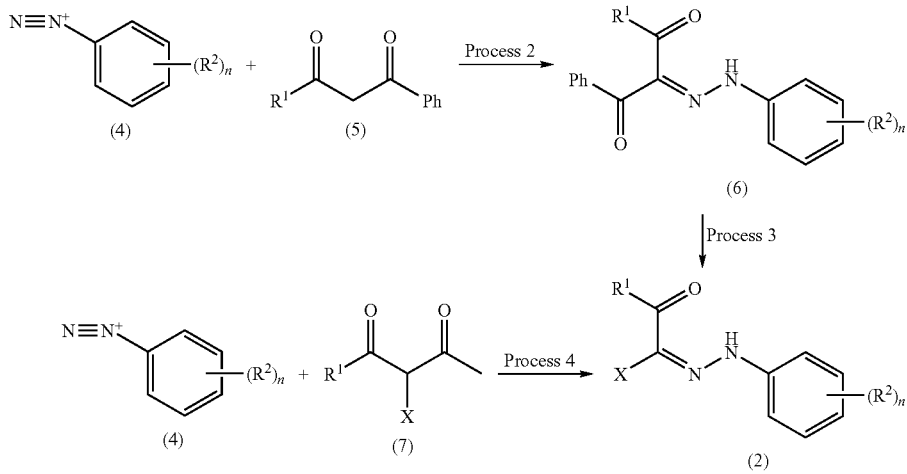

wherein $R^1$, $R^2$, n and X have the same meanings as defined above.

Since the compound of formula (1) selectively antagonize $S1P_3$ receptors as shown in the Test Examples described below, a medicine containing the compound can be used, for example, as a therapeutic agent or prophylactic agent for arteriosclerosis, intimal thickening, vascular proliferative diseases (solid tumors, diabetic retinopathy and the like), cardiac failure, ischemic reperfusion disorder, cerebrovascular spasm after subarachnoid hemorrhage, angina pectoris or myocardial infarction caused by coronary spasm, progressive renal diseases such as glomerulonephritis, thrombosis, pulmonary diseases caused by pulmonary edema (ARDS or the like), bradycardia, parasympathetic-mediated atrial fibrillation or the like, or as a vasodilator.

The compound of formula (1) of the present invention or the pharmaceutically acceptable salt thereof can be orally or parenterally administered. The dosage form for administration can be formulated with an pharmaceutically acceptable additives such as excipient, a binding agent, a buffering agent, a thickening agent, a stabilizer, an emulsifier, a dispersant, a suspending agent or a preservative by conventional methods.

Examples of preparations for oral administration include tablets (including sugar-coated tablets and film-coated tablets), pills, granules, powders, capsules (including soft capsules), syrups, emulsions, suspensions and the like. These preparations for oral administration can be produced according to known methods, by incorporating additives that are conventionally used in the pharmaceutical field. Examples of such additives include excipients such as lactose, mannitol and anhydrous calcium hydrogen phosphate; binding agents such as hydroxypropylcellulose, methylcellulose and polyvinylpyrrolidone; disintegrants such as starch and carboxymethylcellulose; lubricants such as magnesium stearate and talc; and the like.

In the parenteral manner, administration can be performed by means of injection preparations, rectally administrable preparations, topically administrable preparations and the like. Examples of the injection preparations include sterilized solutions or suspensions, and the like. These injection preparations are prepared, for example, by dissolving or suspending the compound of formula (1) or a pharmaceutically acceptable salt thereof in the water for injection (the Japanese Pharmacopoeia). If necessary, an isotonic agent such as sodium chloride; a buffering agent such as sodium hydrogen phosphate or sodium monohydrogen phosphate; a dissolution aid; and the like may be incorporated. Furthermore, the preparation can also be prepared as a ready-to-use injection preparation (powder filling, lyophilization), and in this case, the production can be performed by conventional methods, by adding excipients such as mannitol and lactose.

The rectally administrable preparations include suppositories and the like. A suppository is produced, for example, by dissolving or suspending the compound of formula (1) or a pharmaceutically acceptable salt thereof in a base such as cacao butter or macrogol, and then forming the mixture by pouring it into a mold. Furthermore, a liquid or cream thus produced may be filled in a container for infusion to be used as a rectally administrable preparation.

The topically administrable preparations may include liquid preparations, eye drops, creams, ointments, gel preparations, spray preparations, powder preparations and the like. The liquid preparation can be prepared by adding the compound of formula (1) or a pharmaceutically acceptable salt thereof to water, and adding a stabilizer, a solubilizing agent, a thickening agent, a dispersant, a suspending agent or the like as necessary. As for this thickening agent, gelatin, sodium hyaluronate, high molecular weight dextran, sodium alginate, sodium chondroitin sulfate or the like can be used. The eye drop can be prepared by adding a buffering agent, a pH adjusting agent and an isotonic agent, as well as a preservative. The cream and the ointment can be prepared with an aqueous or oily base, such as water, liquid paraffin, plant oil (peanut oil, castor oil or the like), macrogol or the like. The gel preparation can be prepared by a known method, using gelatin, pectin, carrageenan, agar, tragacanth gum, alginates, cellulose ethers (methylcellulose, sodium carboxymethylcellulose and the like), pectin derivatives, polyacrylates, polymethacrylates, polyvinyl alcohol, polyvinylpyrrolidone and the like. The spray preparation can be prepared by dissolving or suspending the compound of formula (1) or a pharmaceutically acceptable salt thereof in water or the like, and then filling the solution or suspension in a spray bottle. In the case of using the powder preparation, the compound of formula (1) or a pharmaceutically acceptable salt thereof can be used per se, or can be prepared by mixing with appropriate excipients.

The daily dosage for an adult of the compound of formula (1) may vary with the symptom, body weight or age of the patient, the kind of the compound, administration route or the like, but in the case of oral administration, the dosage is suitably about 0.01 to 1,000 mg, and preferably about 0.1 to 300 mg. In the case of parenteral administration, an amount of one-tenth to one-half of the dose for the oral administration may be administered. These dosages can be appropriately increased or reduced in accordance with the symptoms, body weight or age of the patient.

EXAMPLES

Hereinafter, the present invention will be described in detail by way of Examples, but the present invention is not intended to be limited to these Examples.

Reference Example 1

2-Bromo-2-(4-chlorophenylhydrazono)-acetophenone (Reference Compound 1)

4-Chloroaniline (3.2 g) was dissolved in concentrated hydrochloric acid (5.8 mL) and water (11.6 mL), and the solution was stirred for 15 minutes. Then, ice (30 g) was added thereto, an aqueous solution (4 mL) of sodium nitrite (1.8 g) was added dropwise under ice cooling, and the resulting mixture was stirred for 30 minutes. The reaction solution was returned to room temperature, and an aqueous solution (60 mL) of sodium acetate (6.2 g), and a mixed solution of dibenzoylmethane (5.7 g) in diethyl ether (20 mL)-ethanol (25 mL) were added thereto. The mixture was stirred vigorously for 3 hours. Precipitated yellow crude crystals were collected by filtration, washed with water and then dried under reduced pressure, to obtain (4-chlorophenylhydrazono)dibenzoylmethane (9.5 g) as yellow crystals. To a mixed solution of these crude crystals (9.5 g) and sodium acetate (5.1 g) in acetic acid (60 mL)-acetic anhydride (15 mL), a solution of bromine (1.3 mL) in acetic acid (8.0 mL) was slowly added dropwise under ice cooling. The mixture was stirred for 30 minutes, and then for 16 hours at room temperature. The reaction solution was poured onto ice water (200 mL), and the mixture was stirred for 1 hour. Precipitated crude crystals were collected by filtration, washed with hydrous ethanol and diethyl ether, and dried under reduced pressure, to obtain the title compound (4.4 g) as pale yellow crystals.

$^1$H-NMR (300 MHz, CDCl$_3$) δ: 7.06 (d, J=9.0 Hz, 2H), 7.49 (dd, J=7.3, 7.5 Hz, 2H), 7.60 (t, J=7.3 Hz, 1H), 7.99 (d, J=7.5 Hz, 1H), 8.61 (s, 1H);

m.p.: 190-192° C.

Reference Example 2

Ethyl bromo-(4-chlorophenylhydrazono) acetate (Reference Compound 2)

The title compound (3.2 g) was obtained as yellow crystals by the same method as in Reference Example 1, from 4-chloroaniline (3.2 g) and ethyl benzoylacetate (5.3 g).
$^1$H-NMR (300 MHz, CDCl$_3$) δ: 1.40 (t, J=7.2 Hz, 3H), 4.39 (q, J=7.2 Hz, 2H), 7.17 (d, J=8.8 Hz, 2H), 7.29 (d, J=8.8 Hz, 2H), 8.36 (s, 1H);
m.p.: 129-131° C.

Reference Example 3

[2-Chloro-2-(4-chlorophenylhydrazono)acetyl]piperidine (Reference Compound 3)

6 N hydrochloric acid (18 mL) and water (15 mL) were added to 4-chloroaniline (3.2 g), and the mixture was stirred for 15 minutes. Then, an aqueous solution (10 mL) of sodium nitrite (1.8 g) was added dropwise under ice cooling, and the resulting mixture was stirred for 30 minutes, to prepare a solution of diazonium salt.

2-Chloro-1-(piperidin-1-yl)butane-1,3-dione (6) was dissolved in ethanol (200 mL), an aqueous solution (60 mL) of sodium acetate (6.2 g) was added thereto, and the previously prepared diazonium salt solution was added dropwise under ice cooling. The resulting mixture was vigorously stirred for 4 hours. Water (500 mL) was added to the reaction mixture, and the mixture was extracted with ethyl acetate. The organic layer was dried over anhydrous sodium sulfate, and then the solvent was distilled off under reduced pressure. The obtained crude product was diluted with ethanol (60 mL), and the mixture was heated to reflux for 1 hour. After standing the mixture to cool, the mixture was stirred in an ice bath, and precipitated crude crystals were collected by filtration, washed with petroleum ether, and then dried under reduced pressure, to obtain [2-chloro-2-(4-chloropehnylhydrazono)acetyl]piperidine (5) (5.0 g) as milk white crystals.
$^1$H-NMR (300 MHz, CDCl$_3$) δ: 1.63-1.77 (m, 6H), 3.63-3.70 (m, 4H), 7.01 (d, J=8.8 Hz, 2H), 7.25 (d, J=8.8 Hz, 2H), 7.97 (s, 1H);
m.p.: 154-155° C.

Reference Example 4

N-t-Butyl-[2-chloro-2-(4-chlorophenylhydrazono)]acetamide (Reference Compound 4)

The title compound (5.1 g) was obtained as yellow crystals by the same method as in Reference Example 3, from 4-chloroaniline (3.2 g) and N-t-butyl-(2-acetyl-2-chloro)acetamide (4.8 g).
$^1$H-NMR (300 MHz, CDCl$_3$) δ: 1.45 (s, 9H), 6.57 (brs, 1H), 7.04 (d, J=8.6H z, 2H), 7.29 (d, J=8.6 Hz, 2H), 8.03 (s, 1H);
m.p.: 168-170° C.

Reference Example 5

[1-Chloro-1-(4-chlorophenylhydrazono)]-3,3-dimethyl-2-butan one (Reference Compound 5)

The title compound (0.6 g) was obtained as yellow crystals by the same method as in Reference Example 3, from 4-chloroaniline (0.6 g) and 3-chloro-5,5-dimethylhexane-2,4-dione (0.8 g).

$^1$H-NMR (300 MHz, CDCl$_3$) δ: 1.43 (s, 9H), 7.12 (d, J=8.7 Hz, 2H), 7.33 (d, J=8.7 Hz, 2H), 8.34 (s, 1H);
m.p.: 129-131° C.

Reference Example 6

1-Chloro-(4-chlorophenylhydrazono)-2-hexanone (Reference Compound 6)

The title compound (1.4 g) was obtained as a yellow powder by the same method as in Reference Example 3, from 4-chloroaniline (1.3 g) and 3-chloro-2,4-octanedione (1.9 g).
$^1$H-NMR (300 MHz, CDCl$_3$) δ: 0.95 (t, J=7.3 Hz, 3H), 1.41 (qt, J=7.3, 7.5H z, 2H), 1.70 (tt, J=7.5, 7.5 Hz, 2H), 2.96 (t, J=7.5 Hz, 2H), 7.16 (d, J=8.8 Hz, 2H), 7.35 (d, J=8.8 Hz, 2H), 8.39 (s, 1H);
m.p.: 117-119° C.

Reference Example 7

1-Chloro-1-(4-chlorophenylhydrazono)-3-ethyl-2-pentanone (Reference Compound 7)

The title compound (2.0 g) was obtained as a milk white powder by the same method as in Reference Example 3, from 4-chloroaniline (2.9 g) and 3-chloro-5-ethyl-2,4-heptanedione (4.3 g).
$^1$H-NMR (300 MHz, CDCl$_3$) δ: 0.89 (t, J=7.5 Hz, 3H), 1.52-1.83 (m, 4H), 3.44-3.52 (m, 1H), 7.16 (d, J=9.0 Hz, 2H), 7.34 (d, J=9.0 Hz, 2H), 8.43 (s, 1H).

Reference Example 8

1-Chloro-1-(4-chlorophenylhydrazono)-4,4-dimethyl-2-pentanone (Reference Compound 8)

The title compound (2.1 g) was obtained as a yellow powder by the same method as in Reference Example 3, from 4-chloroaniline (1.8 g) and 3,6-dichloro-5,5-dimethyl-2,4-hexanedione (2.6 g)
$^1$H-NMR (300 MHz, CDCl$_3$) δ: 1.06 (s, 9H), 2.88 (s, 2H), 7.15 (d, J=8.9 Hz, 2H), 7.34 (d, J=8.9 Hz, 2H), 8.39 (s, 1H).

Reference Example 9

2-(4-Chlorophenylhydrazono)-2-chloro-1-(2-furyl)ethanone (Reference Compound 9)

The title compound (3.3 g) was obtained as a yellow powder by the same method as in Reference Example 3, from 4-chloroaniline (3.0 g) and 2-chloro-1-(2-furyl)-1,3-butanedione (4.4 g).
$^1$H-NMR (300 MHz, CDCl$_3$) δ: 6.63-6.64 (m, 1H), 7.16 (d, J=9.0 Hz, 2H), 7.36 (d, J=9.0 Hz, 2H), 7.60-7.62 (m, 1H), 7.74-7.75 (m, 1H), 8.56 (s, 1H).

Reference Example 10

1-(4-Chlorophenylhydrazono)-1,4-dichloro-3,3-dimethyl-2-butanone (Reference Compound 10)

The title compound (1.6 g) was obtained as a yellow powder by the same method as in Reference Example 3, from 4-chloroaniline (1.3 g) and 3,6-dichloro-5,5-dimethyl-2,4-hexanedione (2.2 g).
$^1$H-NMR (300 MHz, CDCl$_3$) δ: 1.50 (s, 6H), 3.99 (s, 2H), 7.10 (d, J=8.9 Hz, 2H), 7.35 (d, J=8.9 Hz, 2H), 8.41 (s, 1H).

Reference Example 11

1-Chloro-1-(3,4-dichlorophenylhydrazono)-3,3-dimethyl-2-butanone (Reference Compound 11)

The title compound (1.8 g) was obtained as an orange powder by the same method as in Reference Example 3, from 3,4-dichloroaniline (2.6 g) and 3-chloro-5,5-dimethylhexane-2,4-dione (1.8 g).

$^1$H-NMR (300 MHz, CDCl$_3$) δ: 1.43 (s, 9H), 7.02 (dd, J=2.6, 8.8 Hz, 1H), 7.28 (d, J=2.6 Hz, 1H), 7.41 (d, J=8.8 Hz, 1H), 8.31 (s, 1H);

MS (APCI) m/z 303 (M−Cl+MeOH)$^+$;

m.p.: 134-136° C.

Reference Example 12

1-Chloro-1-(4-chlorophenylhydrazono)-2-(2-thienyl)-2-ethanone (Reference Compound 12)

The title compound (0.9 g) was obtained as a yellow powder by the same method as in Reference Example 3, from 4-chloroaniline (1.5 g) and 2-chloro-1-(2-thienyl)-1,3-butanedione (2.4 g).

$^1$H-NMR (300 MHz, CDCl$_3$) δ: 7.20-7.26 (m, 3H), 7.37 (d, J=8.7 Hz, 2H), 7.75 (s, 1H), 8.19 (s, 1H), 8.55 (s, 1H).

Example 1

2-(4-Chlorophenylhydrazono)-2-(3-fluorophenylamino)acetophenone (Compound 1)

The Reference Compound 1 (169 mg) was dissolved in tetrahydrofuran (5 mL), then triethylamine (69 μL) and 3-fluoroaniline (58 μL) were added thereto, and the resulting mixture was stirred for 2 hours at room temperature. The solvent was distilled off under reduced pressure, the residue was diluted with ethyl acetate and water, and the dilution was partitioned. The organic layer was washed with saturated brine and dried over anhydrous sodium sulfate, and then the solvent was distilled off under reduced pressure. The crude product thus obtained was separated and purified by silica gel column chromatography (hexane:ethyl acetate=5:1), to obtain the title compound (126 mg) as an orange-colored amorphous material.

$^1$H-NMR (300 MHz, CDCl$_3$) δ: 6.45 (d, J=10.1 Hz, 1H), 6.52 (d, J=7.9 Hz, 1H), 6.70 (dd, J=7.9, 10.1 Hz, 1H), 6.95 (d, J=8.8 Hz, 2H), 7.03 (s, 1H), 7.23-7.28 (m, 3H), 7.49-7.63 (m, 4H), 8.15 (d, J=7.0 Hz, 2H);

MS (ESI) m/z 366 (M−H)$^-$.

Examples 2 to 20

The compounds of Examples 2 to 20 were obtained in the same manner as in Example 1. The obtained compounds are presented in Tables 1 to 3. However, in Examples 13 to 20, the compounds were synthesized using the Reference Compound 2 instead of the Reference Compound 1.

TABLE 1

| Example | R$^1$ | (R$^2$)$_n$ | D | A + (R$^3$)$_m$ | $^1$H-NMR (300 MHz, CDCl$_3$) | MS |
|---|---|---|---|---|---|---|
| 2 | Ph | 4-Cl | — | 3-CF$_3$-phenyl (methyl-substituted) | 6.82 (d, J = 8.1 Hz, 1H), 6.93-6.99 (m, 3H), 7.14 (s, 1H), 7.21-7.25 (m, 3H), 7.39 (dd, J = 7.7, 7.7 Hz, 1H), 7.49-7.64 (m, 4H), 8.16 (d, J = 7.3 Hz, 2H) | 416 |
| 3 | Ph | 4-Cl | — | 2,3-difluoro-phenyl (methyl-substituted) | 6.20 (dd, J = 7.7, 8.0 Hz, 1H), 6.74-6.83 (m, 1H), 6.90 (s, 1H), 6.93 (d, J = 7.7 Hz, 1H), 6.98 (d, J = 9.0 Hz, 2H), 7.24 (d, J = 9.0 Hz, 2H), 7.51 (dd, J = 7.2, 7.5 Hz, 2H), 7.61 (dd, J = 7.5, 7.5 Hz, 1H), 7.73 (s, 1H), 8.14 (d, J = 7.2 Hz, 2H) | 384 |
| 4 | Ph | 4-Cl | — | 2,6-dichloro-4-methylpyridine | *) 6.61 (s, 2H), 7.18 (d, J = 8.7 Hz, 2H), 7.33 (d, J = 8.7 Hz, 2H), 7.53 (dd, J = 7.2, 7.8 Hz, 2H), 7.63 (dd, J = 7.2, 7.2 Hz, 1H), 7.97 (d, J = 7.8 Hz, 2H) | 417 |
| 5 | Ph | 4-Cl | CH$_2$ | 4-fluoro-methylphenyl | 4.21 (d, J = 4.8 Hz, 2H), 5.33 (brs, 1H), 6.82 (d, J = 8.8 Hz, 2H), 7.04-7.09 (m, 2H), 7.20 (d, J = 8.8 Hz, 2H), 7.35-7.39 (m, 2H), 7.46 (dd, J = 7.2, 7.9 Hz, 2H), 7.55 (dd, J = 7.2, 7.2 Hz, 1H), 7.71 (s, 1H), 8.00 (d, J = 7.9 Hz, 2H) | 380 |

TABLE 1-continued

| Example | R¹ | (R²)$_n$ | D | A + (R³)$_m$ | ¹H-NMR (300 MHz, CDCl₃) | MS |
|---|---|---|---|---|---|---|
| 6 | Ph | 4-Cl | CH₂ | 2,4-difluorophenyl | 4.18 (d, J = 7.7 Hz, 2H), 5.04 (t, J = 7.7 Hz, 1H), 6.98 (d, J = 8.8 Hz, 2H), 7.01-7.16 (m, 3H), 7.24 (d, J = 8.8 Hz, 2H), 7.46 (dd, J = 7.2, 7.7 Hz, 2H), 7.56 (dd, J = 7.2, 7.2 Hz, 1H), 8.04 (d, J = 7.7 Hz, 2H), 8.19 (s, 1H) | 398 |
| 7 | Ph | 4-Cl | CH₂ | 3-(trifluoromethyl)phenyl | 4.30 (d, J = 7.3 Hz, 2H), 5.31 (t, J = 7.3 Hz, 1H), 6.83 (d, J = 8.8 Hz, 2H), 7.20 (d, J = 8.8 Hz, 2H), 7.42-7.61 (m, 6H), 7.68 (d, J = 9.9 Hz, 2H), 8.00 (d, J = 8.6 Hz, 2H) | 430 |
| 8 | Ph | 4-Cl | — | 2-fluorophenyl | 6.39-6.45 (m, 1H), 6.90-7.04 (m, 5H), 7.11-7.25 (m, 3H), 7.51 (dd, J = 6.8, 7.8 Hz, 2H), 7.60 (dd, J = 6.8, 6.8 Hz, 1H), 7.64 (s, 1H), 8.14 (d, J = 7.8 Hz, 2H) | 366 |

*) DMSO-d6 was used as the solvent for measurement.

TABLE 2

| Example | R¹ | (R²)$_n$ | D | A + (R³)$_m$ | ¹H-NMR (300 MHz, CDCl₃) | MS |
|---|---|---|---|---|---|---|
| 9 | Ph | 4-Cl | — | 4-fluorophenyl | 6.70-6.74 (m, 2H), 6.90 (d, J = 8.8 Hz, 2H), 6.98-7.03 (m, 3H), 7.21 (d, J = 8.8 Hz, 2H), 7.40 (s, 1H), 7.51 (dd, J = 7.2, 7.8 Hz, 2H), 7.61 (dd, J = 7.2, 7.2 Hz, 1H), 8.15 (d, J = 7.8 Hz, 2H) | 366 |
| 10 | Ph | 4-Cl | — | 2-chlorophenyl | 6.38 (d, J = 7.9 Hz, 1H), 6.92 (dd, J = 7.7, 7.9 Hz, 1H), 6.96 (d, J = 8.8 Hz, 2H), 7.11 (s, 1H), 7.15 (dd, J = 7.7, 7.8 Hz, 1H), 7.22 (d, J = 8.8 Hz, 2H), 7.43 (d, J = 7.8 Hz, 1H), 7.51 (dd, J = 7.2, 8.2 Hz, 2H), 7.61 (dd, J = 7.2, 7.2 Hz, 1H), 7.63 (s, 1H), 8.15 (d, J = 8.2 Hz, 2H) | 382 |
| 11 | Ph | 4-Cl | — | 3-chlorophenyl | 6.58 (d, J = 6.1 Hz, 1H), 6.75 (s, 1H), 6.93-7.01 (m, 4H), 7.18-7.24 (m, 3H), 7.51 (dd, J = 7.2, 8.1 Hz, 2H), 7.53 (s, 1H), 7.61 (dd, J = 7.2, 7.2 Hz, 1H), 8.15 (d, J = 8.1 Hz, 2H) | 382 |
| 12 | Ph | 4-Cl | — | 4-chlorophenyl | 6.67 (d, J = 8.5 Hz, 2H), 6.93 (d, J = 8.9 Hz, 2H), 7.03 (s, 1H), 7.22 (d, J = 8.9 Hz, 2H), 7.25 (d, J = 8.5 Hz, 2H), 7.43 (s, 1H), 7.51 (dd, J = 7.2, 7.8 Hz, 2H), 7.61 (dd, J = 7.2, 7.2 Hz, 1H), 8.15 (d, J = 7.8 Hz, 2H) | 382 |

TABLE 2-continued
| Example | R¹ | (R²)ₙ | D | A + (R³)ₘ | ¹H-NMR (300 MHz, CDCl₃) | MS |
|---|---|---|---|---|---|---|
| 13 | EtO | 4-Cl | — |  | 1.38-1.47 (m, 3H), 4.33-4.47 (m, 2H), 6.37-6.44 (m, 2H), 6.60-6.70 (m, 1H), 7.00 (s, 1H), 7.04 (d, J = 8.8 Hz, 2H), 7.07-7.26 (m, 1H), 7.23 (d, J = 8.8 Hz, 2H), 7.46 (s, 1H) | 334 |
| 14 | EtO | 4-Cl | — |  | 1.39-1.47 (m, 3H), 4.33-4.47 (m, 2H), 6.39 (s, 1H), 6.59 (d, J = 8.6 Hz, 2H), 7.02 (d, J = 9.0 Hz, 2H), 7.01-7.31 (m, 5H) | 350 |
| 15 | EtO | 4-Cl | CH₂ | 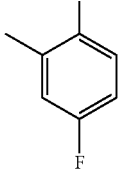 | 1.34-1.42 (m, 3H), 4.30-4.43 (m, 4H), 4.71 (s, 1H), 6.84 (d, J = 8.8 Hz, 2H), 6.87-7.15 (m, 3H), 7.14 (d, J = 8.8 Hz, 2H), 10.45 (s, 1H) | 366 |
| 16 | EtO | 4-Cl | — |  | 1.39-1.48 (m, 3H), 4.34-4.49 (m, 2H), 6.46 (s, 0.5H), 6.67 (s, 0.5H), 6.75 (d, J = 7.7 Hz, 0.5H), 6.92 (s, 0.5H), 7.01-7.06 (m, 2H), 7.18-7.26 (m, 3H), 7.35-7.49 (m, 2H), 8.02 (s, 0.5H), 10.85 (s, 1H) | 384 |
| 17 | EtO | 4-Cl | — | 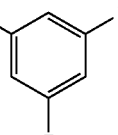 | 1.38-1.47 (m, 3H), 4.33-4.48 (m, 2H), 6.17-6.19 (m, 1H), 6.26 (s, 0.5H), 6.37-6.45 (m, 1H), 6.62 (s, 0.5H), 7.00-7.10 (m, 3H), 7.24-7.26 (m, 2H), 7.58 (s, 0.5H), 10.92 (s, 0.5H) | 352 |
TABLE 3
| Example | R¹ | (R²)ₙ | D | A + (R³)ₘ | ¹H-NMR (300 MHz, CDCl₃) | MS |
|---|---|---|---|---|---|---|
| 18 | EtO | 4-Cl | — | 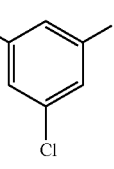 | 1.38-1.47 (m, 3H), 4.33-4.47 (m, 2H), 6.57 (s, 1H), 6.92-7.10 (m, 3H), 7.24-7.27 (m, 2H), 7.43 (s, 2H), 10.88 (s, 1H) | 384 |
| 19 | EtO | 4-Cl | — |  | 1.38-1.47 (m, 3H), 4.33-4.46 (m, 2H), 6.45 (s, 1H), 6.65-6.67 (m, 2H), 6.96-7.01 (m, 3H), 7.18-7.29 (m, 4H), 7.34 (s, 1H) | 316 |
| 20 | EtO | 4-Cl | — |  | 1.39-1.48 (m, 3H), 4.34-4.49 (m, 2H), 6.36 (s, 0.5H), 6.63 (s, 0.5H), 6.80-6.83 (m, 0.5H), 6.92 (s, 0.5H), 6.99-7.08 (m, 2H), 7.21-7.27 (m, 3H), 7.33-7.40 (m, 1H), 7.45 (s, 0.5H), 7.62-7.65 (m, 0.5H), 7.85 (s, 0.5H), 10.90 (s, 0.5H) | 341 |

Example 21

[1-(4-Chlorophenylhydrazono)-1-(3-fluorophenylamino)acetyl]piperidine (Compound 21)

The Reference Compound 3 (150 mg) was dissolved in ethanol (5 mL), then triethylamine (84 μL) and 3-fluoroaniline (53 μL) were added thereto, and the resulting mixture was stirred for 2 hours at 50° C. The solvent was distilled off under reduced pressure, the residue was diluted with ethyl acetate and water, and extracted with ethyl acetate. The organic layer was washed with saturated brine and dried over anhydrous sodium sulfate, and the solvent was distilled off under reduced pressure. The crude crystals thus obtained were washed with a solvent mixture of hexane-ethyl acetate (20:1), and dried under reduced pressure, to obtain the title compound (123 mg) as orange-colored crystals.

$^1$H-NMR (300 MHz, CDCl$_3$) δ: 1.65-1.78 (m, 6H), 3.67 (brs, 2H), 4.02 (brs, 2H), 6.34-6.38 (m, 1H), 6.44-6.47 (m, 1H), 6.61-6.68 (m, 1H), 6.91 (d, J=8.8 Hz, 2H), 7.07-7.08 (m, 2H), 7.19 (d, J=8.8 Hz, 2H), 7.21 (s, 1H);

MS (ESI) m/z 373 (M-H)$^-$.

Examples 22 to 129

The compounds of Examples 22 to 141 were obtained in the same manner as in Example 21, using the Reference Compounds 3 to 12 or compounds obtained in the same manner as in Reference Example 3, and the corresponding anilines. The obtained compounds are presented in Tables 4 to 17.

TABLE 4

| Example | R$^1$ | (R$^2$)$_n$ | D | A + (R$^3$)$_m$ | $^1$H-NMR (300 MHz, CDCl$_3$) | MS |
|---|---|---|---|---|---|---|
| 22 | piperidinyl | 4-Cl | — | 3,5-diCl-phenyl | 1.61-1.79 (m, 6H), 3.67 (brs, 2H), 4.00 (brs, 2H), 6.50 (s, 2H), 6.90-6.93 (m, 3H), 7.19-7.26 (m, 4H) | 423 |
| 23 | piperidinyl | 4-Cl | — | 4-Cl-phenyl | 1.60-1.77 (m, 6H), 3.66 (brs, 2H), 4.00 (brs, 2H), 6.59 (d, J = 8.6 Hz, 2H), 6.89 (d, J = 8.8 Hz, 2H), 6.97 (s, 1H), 7.06 (s, 1H), 7.19 (d, J = 8.6 Hz, 2H), 7.20 (d, J = 8.8 Hz, 2H) | 389 |
| 24 | piperidinyl | 4-Cl | — | 3-Cl-phenyl | 1.60-1.77 (m, 6H), 3.66 (brs, 2H), 4.00 (brs, 2H), 6.52 (d, J = 8.1 Hz, 1H), 6.66 (s, 1H), 6.89-6.93 (m, 3H), 7.07 (s, 2H), 7.18 (dd, J = 8.1, 8.1 Hz, 1H), 7.20 (d, J = 8.8 Hz, 2H) | 389 |
| 25 | piperidinyl | 4-Cl | — | 3,5-diF-phenyl | 1.61-1.78 (m, 6H), 3.67 (brs, 2H), 4.01 (brs, 2H), 6.14-6.20 (m, 2H), 6.35-6.42 (m, 1H), 6.93 (d, J = 8.8 Hz, 2H), 7.13 (s, 1H), 7.21 (d, J = 8.8 Hz, 2H), 7.24 (s, 1H) | 391 |
| 26 | piperidinyl | 4-Cl | — | 3,4-diCl-phenyl | 1.62-1.79 (m, 6H), 3.67 (brs, 2H), 4.01 (brs, 2H), 6.49 (dd, J = 2.6, 8.6 Hz, 1H), 6.74 (d, J = 2.6 Hz, 1H), 6.91 (d, J = 8.8 Hz, 2H), 7.07 (s, 1H), 7.11 (s, 1H), 7.21 (d, J = 8.8 Hz, 2H), 7.27 (d, J = 8.6 Hz, 1H) | 423 |
| 27 | piperidinyl | 4-Cl | — | 3-CN-phenyl | 1.60-1.77 (m, 6H), 3.68 (brs, 2H), 4.03 (brs, 2H), 6.84-6.92 (m, 4H), 7.07 (s, 1H), 7.20-7.26 (m, 4H), 7.30-7.36 (m, 1H) | 380 |

TABLE 4-continued

| Example | R¹ | (R²)ₙ | D | A + (R³)ₘ | ¹H-NMR (300 MHz, CDCl₃) | MS |
|---|---|---|---|---|---|---|
| 28 | t-Bu-NH- | 4-Cl | — | 3-F-phenyl | 1.46 (s, 9H), 6.36-6.48 (m, 2H), 6.67-6.76 (m, 2H), 6.88 (d, J = 8.8 Hz, 2H), 7.03 (s, 1H), 7.17-7.31 (m, 2H), 7.21 (d, J = 8.8 Hz, 2H) | 361 |
| 29 | t-Bu-NH- | 4-Cl | — | 4-Cl-phenyl | 1.46 (s, 9H), 6.59 (s, 1H), 6.61 (d, J = 8.8 Hz, 2H), 6.85 (d, J = 8.8 Hz, 2H), 7.05 (s, 1H), 7.20 (d, J = 8.8 Hz, 2H), 7.22 (d, J = 8.8 Hz, 2H), 7.21 (s, 1H) | 377 |

TABLE 5

| Example | R¹ | (R²)ₙ | D | A + (R³)ₘ | ¹H-NMR (300 MHz, CDCl₃) | MS |
|---|---|---|---|---|---|---|
| 30 | t-Bu-NH- | 4-Cl | — | 3,5-diCl-phenyl | 1.46 (s, 9H), 6.52 (s, 2H), 6.74 (s, 1H), 6.92 (d, J = 8.7 Hz, 2H), 6.96 (s, 1H), 6.98 (s, 1H), 7.20 (s, 1H), 7.23 (d, J = 8.7 Hz, 2H) | 411 |
| 31 | t-Bu-NH- | 4-Cl | — | 3,4-diCl-phenyl | 1.46 (s, 9H), 6.49 (dd, J = 2.6, 8.7 Hz, 1H), 6.64 (s, 1H), 6.76 (d, J = 2.6 Hz, 1H), 6.89 (d, J = 8.8 Hz, 2H), 7.01 (s, 1H), 7.22 (d, J = 8.8 Hz, 2H), 7.26 (s, 1H), 7.30 (d, J = 8.7 Hz, 1H) | 411 |
| 32 | t-Bu | 4-Cl | — | 3-F-phenyl | 1.48 (s, 9H), 6.29-6.35 (m, 1H), 6.39-6.42 (m, 1H), 6.62-6.69 (m, 1H), 6.75 (s, 1H), 7.01 (d, J = 8.9 Hz, 2H), 7.16-7.26 (m, 3H), 7.38 (s, 1H) | 346 |
| 33 | t-Bu | 4-Cl | — | 4-Cl-phenyl | 1.48 (s, 9H), 6.55 (d, J = 8.4 Hz, 2H), 6.76 (s, 1H), 6.98 (d, J = 8.8 Hz, 2H), 7.19-7.26 (m, 5H) | 362 |
| 34 | t-Bu | 4-Cl | — | 3,5-diF-phenyl | 1.47 (s, 9H), 6.10-6.17 (m, 2H), 6.37-6.43 (m, 1H), 6.68 (s, 1H), 7.04 (d, J = 8.9 Hz, 2H), 7.27 (d, J = 8.9 Hz, 2H), 7.48 (s, 1H) | 364 |

TABLE 5-continued

| Example | R¹ | (R²)$_n$ | D | A + (R³)$_m$ | ¹H-NMR (300 MHz, CDCl₃) | MS |
|---|---|---|---|---|---|---|
| 35 | t-Bu | 4-Cl | — | 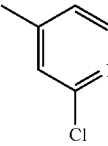 | 1.46 (s, 9H), 6.42 (s, 2H), 7.00 (s, 1H), 7.12 (d, J = 8.8 Hz, 2H), 7.30 (d, J = 8.8 Hz, 2H), 7.86 (s, 1H) | 397 |
| 36 | t-Bu | 4-Cl | — | 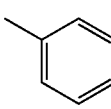 | 1.49 (s, 9H), 6.68 (d, J = 7.9 Hz, 1H), 6.83 (s, 1H), 6.90 (s, 1H), 7.01 (d, J = 8.6 Hz, 2H), 7.19-7.38 (m, 3H), 7.25 (d, J = 8.6 Hz, 2H) | 396 |
| 37 | t-Bu | 4-Cl | — | 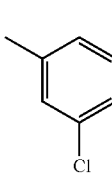 | 1.48 (s, 9H), 6.48 (s, 2H), 6.67 (s, 1H), 6.93-6.95 (m, 1H), 7.04 (d, J = 9.1 Hz, 2H), 7.27 (d, J = 9.1 Hz, 2H), 7.41 (s, 1H) | 396 |
| 38 | t-Bu | 4-Cl | — | 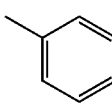 | 1.48 (s, 9H), 6.42 (dd, J = 2.6, 8.6 Hz, 1H), 6.70 (s, 1H), 6.73 (d, J = 2.6 Hz, 1H), 7.02 (d, J = 8.8 Hz, 2H), 7.26 (d, J = 8.8 Hz, 2H), 7.29 (d, J = 8.6 Hz, 2H), 7.26 (s, 1H) | 396 |
| 39 | t-Bu | 4-Cl | CH₂ | 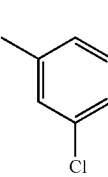 | 1.36 (s, 9H), 4.04 (d, J = 7.5 Hz, 2H), 5.11 (t, J = 7.5 Hz, 1H), 6.94 (d, J = 8.7 Hz, 2H), 7.19 (s, 2H), 7.25 (d, J = 8.7 Hz, 2H), 7.30 (s, 1H), 7.49 (s, 1H) | 410 |

TABLE 6

| Example | R¹ | (R²)$_n$ | D | A + (R³)$_m$ | ¹H-NMR (300 MHz, CDCl₃) | MS |
|---|---|---|---|---|---|---|
| 40 | t-Bu | 4-Cl | — | 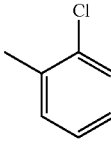 | 1.48 (s, 9 H), 6.14 (d, J = 8.6 Hz, 1 H), 6.80 (s, 1 H), 7.03 (d, J = 9.0 Hz, 2 H), 7.08 (dd, J = 2.2, 8.6 Hz, 1 H), 7.27 (d, J = 9.0 Hz, 2 H), 7.41 (d, J = 2.2 Hz, 1 H), 7.42 (s, 1 H) | 396 |
| 41 | t-Bu | 3-Cl | — | 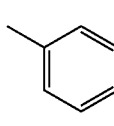 | 1.49 (s, 9 H), 6.31-6.36 (m, 1 H), 6.40-6.43 (m, 1 H), 6.64-6.70 (m, 1 H), 6.77 (s, 1 H), 6.93 (d, J = 8.1 Hz, 2 H), 7.08 (s, 1 H), 7.16-7.24 (m, 2 H), 7.37 (s, 1 H) | 346 |
| 42 | t-Bu | 3-Cl | — | 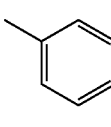 | 1.49 (s, 9 H), 6.55 (d, J = 8.6 Hz, 2 H), 6.78 (s, 1 H), 6.91 (dd, J = 7.4, 7.9 Hz, 2 H), 7.06 (s, 1 H), 7.17-7.25 (m, 4 H) | 362 |
| 43 | t-Bu | 3-Cl | — | 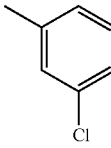 | 1.48 (s, 9 H), 6.48 (s, 2 H), 6.67 (s, 1 H), 6.95-6.97 (m, 3 H), 7.12 (s, 1 H), 7.20-7.27 (m, 1 H), 7.40 (s, 1 H) | 396 |

TABLE 6-continued

| Example | R¹ | (R²)ₙ | D | A + (R³)ₘ | ¹H-NMR (300 MHz, CDCl₃) | MS |
|---|---|---|---|---|---|---|
| 44 | t-Bu | 3-Cl | — | 2,4-diCl-phenyl | 1.48 (s, 9 H), 6.42 (dd, J = 2.7, 8.6 Hz, 1 H), 6.72 (s, 1 H), 6.74 (d, J = 2.7 Hz, 1 H), 6.94 (ddd, J = 2.0, 6.9, 8.1 Hz, 2 H), 7.10 (dd, J = 2.0, 2.0 Hz, 1 H), 7.21 (dd, J = 6.9, 8.1 Hz, 1 H), 7.29 (d, J = 8.6 Hz, 1 H), 7.31 (s, 1 H) | 396 |
| 45 | t-Bu | 2-Cl | — | 3-F-phenyl | 1.50 (s, 9 H), 6.36-6.41 (m, 1 H), 6.45-6.49 (m, 1 H), 6.64-6.71 (m, 1 H), 6.87 (dd, J = 7.3, 8.0 Hz, 1 H), 6.95 (s, 1 H), 7.17-7.31 (m, 3 H), 7.55 (d, J = 8.0 Hz, 1 H), 7.70 (s, 1 H) | 346 |
| 46 | t-Bu | 2-Cl | — | 4-Cl-phenyl | 1.50 (s, 9 H), 6.62 (d, J = 8.6 Hz), 6.87 (dd, J = 7.3, 8.1 Hz, 1 H), 6.93 (s, 1 H), 7.21-7.30 (m, 4 H), 7.54 (d, J = 7.3 Hz, 1 H), 7.61 (s, 1 H) | 362 |
| 47 | t-Bu | 2-Cl | — | 3,5-diCl-phenyl | 1.50 (s, 9 H), 6.53 (s, 2 H), 6.87 (s, 1 H), 6.91 (dd, J = 7.3, 7.9 Hz, 1 H), 6.97 (s, 1 H), 7.26-7.32 (m, 2 H), 7.56 (d, J = 7.9 Hz, 1 H), 7.70 (s, 1 H) | 396 |
| 48 | t-Bu | 2-Cl | — | 3,4-diCl-phenyl | 1.50 (s, 9 H), 6.49 (dd, J = 2.6, 8.6 Hz, 1 H), 6.78 (d, J = 2.6 Hz, 1 H), 6.87 (s, 1 H), 6.87-6.93 (m, 1 H), 7.24-7.27 (m, 2 H), 7.31 (d, J = 8.6 Hz, 1 H), 7.55 (dd, J = 1.3, 8.1 Hz, 1H), 7.66 (s, 1 H) | 396 |

TABLE 7

| Example | R¹ | (R²)ₙ | D | A + (R³)ₘ | ¹H-NMR (300 MHz, CDCl₃) | MS |
|---|---|---|---|---|---|---|
| 49 | t-Bu | H | — | 3-F-phenyl | 1.49 (s, 9 H), 6.31-6.36 (m, 1 H), 6.40-6.43 (m, 1 H), 6.61-6.67 (m, 1 H), 6.70 (s, 1 H), 6.98 (dd, J = 7.5, 7.5 Hz, 1 H), 7.09 (d, J = 8.1 Hz, 2 H), 7.18 (dd, J = 7.9, 7.9 Hz, 1 H), 7.30 (dd, J = 7.5, 8.1 Hz, 2 H), 7.46 (s, 1 H) | 312 |
| 50 | t-Bu | H | — | 4-Cl-phenyl | 1.49 (s, 9 H), 6.56 (d, J = 8.5 Hz, 2 H), 6.71 (s, 1 H), 6.97 (dd, J = 7.3, 7.3 Hz, 1 H), 7.07 (d, J = 7.7 Hz, 2 H), 7.20 (d, J = 8.5 Hz, 2 H), 7.30 (dd, J = 7.3, 7.7 Hz, 2 H), 7.33 (s, 1 H) | 328 |
| 51 | t-Bu | H | — | 3,5-diCl-phenyl | 1.48 (s, 9 H), 6.48 (s, 2 H), 6.58 (s, 1 H), 6.93 (s, 1 H), 7.01 (dd, J = 7.3, 7.3 Hz, 1 H), 7.12 (d, J = 7.5 Hz, 2 H), 7.32 (dd, J = 7.3, 7.5 Hz, 2 H), 7.50 (s, 1 H) | 362 |

TABLE 7-continued

| Example | R¹ | (R²)ₙ | D | A + (R³)ₘ | ¹H-NMR (300 MHz, CDCl₃) | MS |
|---|---|---|---|---|---|---|
| 52 | t-Bu | H | — |  | 1.49 (s, 9 H), 6.42 (dd, J = 2.6, 8.6 Hz, 1 H), 6.64 (s, 1 H), 6.75 (d, J = 2.6 Hz, 1 H), 7.00 (dd, J = 7.3, 7.3 Hz, 1 H), 7.10 (d, J = 7.5 Hz, 2 H), 7.28 (d, J = 8.6 Hz, 1 H), 7.33 (dd, J = 7.3, 7.5 Hz, 2 H), 7.40 (s, 1 H) | 362 |
| 53 | t-Bu | 4-F | — |  | 1.48 (s, 9 H), 6.29-6.34 (m, 1 H), 6.40-6.43 (m, 1 H), 6.62-6.71 (m, 1 H), 6.71 (s, 1 H), 6.97-7.06 (m, 4 H), 7.15-7.23 (m, 1 H), 7.40 (s, 1 H) | 330 |
| 54 | t-Bu | 4-F | — |  | 1.48 (s, 9 H), 6.57-6.61 (m, 2 H), 6.72 (s, 1 H), 6.92-7.00 (m, 6 H), 7.23 (s, 1 H) | 330 |
| 55 | t-Bu | 4-F | — |  | 1.48 (s, 9 H), 6.55 (d, J = 8.8 Hz, 2 H), 6.72 (s, 1 H), 7.00-7.01 (m, 4 H), 7.20 (d, J = 8.8 Hz, 2 H), 7.26 (s, 1 H) | 346 |
| 56 | t-Bu | 4-F | — |  | 1.48 (s, 9 H), 6.50 (d, J = 8.8 Hz, 2 H), 6.70 (s, 1 H), 6.99-7.02 (m, 4 H), 7.27 (s, 1 H), 7.34 (d, J = 8.8 Hz, 2 H) | 390 |
| 57 | t-Bu | 4-F | — |  | 1.49 (s, 9 H), 3.76 (s, 3 H), 6.62 (d, J = 8.8 Hz, 2 H), 6.74 (s, 1 H), 6.81 (d, J = 8.8 Hz, 2 H), 6.95-6.97 (m, 4 H), 7.20 (s, 1 H) | 342 |
| 58 | t-Bu | 4-F | — |  | 1.48 (s, 9 H), 6.66 (d, J = 8.6 Hz, 2 H), 6.78 (s, 1 H), 6.98-7.08 (m, 4 H), 7.37 (s, 1 H), 7.50 (d, J = 8.6 Hz, 2 H) | 380 |

TABLE 8

| Example | R¹ | (R²)ₙ | D | A + (R³)ₘ | ¹H-NMR (300 MHz, CDCl₃) | MS |
|---|---|---|---|---|---|---|
| 59 | t-Bu | 4-F | — | 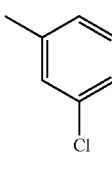 | 1.48 (s, 9 H), 6.47 (d, J = 1.7 Hz, 2 H), 6.62 (s, 1 H), 6.93 (d, J = 1.7 Hz, 1 H), 6.99-7.10 (m, 4 H), 7.42 (s, 1 H) | 380 |
| 60 | t-Bu | 4-F | — | 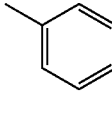 | 1.48 (s, 9 H), 6.42 (dd, J = 2.6, 8.7 Hz, 1 H), 6.66 (s, 1 H), 6.73 (d, J = 2.6 Hz, 1 H), 6.98-7.07 (m, 4 H), 7.28 (d, J = 8.7 Hz, 1 H), 7.33 (s, 1 H) | 380 |
| 61 | t-Bu | 4-Me | — | 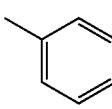 | 1.48 (s, 9 H), 2.30 (s, 3 H), 6.29-6.34 (m, 1 H), 6.38-6.42 (m, 1 H), 6.60-6.65 (m, 2 H), 6.99 (d, J = 8.4 Hz, 2 H), 7.11 (d, J = 8.4 Hz, 2 H), 7.13-7.21 (m, 1 H), 7.44 (s, 1 H) | 326 |

TABLE 8-continued

| Example | R¹ | (R²)ₙ | D | A + (R³)ₘ | ¹H-NMR (300 MHz, CDCl₃) | MS |
|---|---|---|---|---|---|---|
| 62 | t-Bu | 4-Me | — | 4-Cl-C₆H₄ | 1.48 (s, 9 H), 2.30 (s, 3 H), 6.54 (d, J = 8.8 Hz, 2 H), 6.67 (s, 1 H), 6.98 (d, J = 8.4 Hz, 2 H), 7.10 (d, J = 8.4 Hz, 2 H), 7.19 (d, J = 8.8 Hz, 2 H), 7.31 (s, 1 H) | 342 |
| 63 | t-Bu | 4-Me | — | 4-Me-C₆H₄ | 1.48 (s, 9 H), 2.27 (s, 3 H), 2.29 (s, 3 H), 6.54 (d, J = 8.4 Hz, 2 H), 6.67 (s, 1 H), 6.95 (d, J = 8.4 Hz, 2 H), 7.03 (d, J = 8.4 Hz, 2 H), 7.08 (d, J = 8.4 Hz, 2 H), 7.33 (s, 1 H) | 322 |
| 64 | t-Bu | 4-Me | — | 3,5-Cl₂-C₆H₃ | 1.48 (s, 9 H), 2.31 (s, 3 H), 6.47 (d, J = 1.7 Hz, 2 H), 6.56 (s, 1 H), 6.92 (t, J = 1.7 Hz, 1 H), 7.03 (d, J = 8.4 Hz, 2 H), 7.13 (d, J = 8.4 Hz, 2 H), 7.48 (s, 1 H) | 376 |
| 65 | t-Bu | 4-Me | — | 2,4-Cl₂-C₆H₃ | 1.48 (s, 9 H), 2.31 (s, 3 H), 6.41 (dd, J = 2.7, 8.6 Hz, 1 H), 6.60 (s, 1 H), 6.73 (d, J = 2.7 Hz, 1 H), 7.00 (d, J = 8.4 Hz, 2 H), 7.12 (d, J = 8.4 Hz, 2 H), 7.26 (d, J = 8.6 Hz, 1 H), 7.38 (s, 1 H) | 376 |
| 66 | t-Bu | 4-CF₃ | — | 3-F-C₆H₄ | 1.49 (s, 9 H), 6.33-6.38 (m, 1 H), 6.41-6.44 (m, 1 H), 6.65-6.71 (m, 1 H), 6.84 (s, 1 H), 7.12 (d, J = 8.6 Hz, 2 H), 7.17-7.25 (m, 1 H), 7.47 (s, 1 H), 7.54 (d, J = 8.6 Hz, 2 H) | 380 |
| 67 | t-Bu | 4-CF₃ | — | 4-F-C₆H₄ | 1.50 (s, 9 H), 6.61-6.65 (m, 2 H), 6.86 (s, 1 H), 6.94-7.00 (m, 2 H), 7.07 (d, J = 8.5 Hz, 2 H), 7.31 (s, 1 H), 7.52 (d, J = 8.5 Hz, 2 H) | 380 |
| 68 | t-Bu | 4-CF₃ | — | 4-Cl-C₆H₄ | 1.49 (s, 9 H), 6.57 (d, J = 8.6 Hz, 2 H), 6.85 (s, 1 H), 7.10 (d, J = 8.4 Hz, 2 H), 7.21 (d, J = 8.6 Hz, 2 H), 7.34 (s, 1 H), 7.53 (d, J = 8.4 Hz, 2 H) | 396 |

TABLE 9

| Example | R¹ | (R²)ₙ | D | A + (R³)ₘ | ¹H-NMR (300 MHz, CDCl₃) | MS |
|---|---|---|---|---|---|---|
| 69 | t-Bu | 4-CF₃ | — | 4-Br-C₆H₄ | 1.49 (s, 9 H), 6.52 (d, J = 8.5 Hz, 2 H), 6.83 (s, 1 H), 7.11 (d, J = 8.3 Hz, 2 H), 7.35 (s, 1 H), 7.36 (d, J = 8.5 Hz, 2 H), 7.54 (d, J = 8.3 Hz, 2 H) | 440 |
| 70 | t-Bu | 4-CF₃ | — | 4-CF₃-C₆H₄ | 1.50 (s, 9 H), 6.68 (d, J = 8.4 Hz, 2 H), 6.91 (s, 1 H), 7.14 (d, J = 8.4 Hz, 2 H), 7.45 (s, 1 H), 7.51 (d, J = 8.4 Hz, 2 H), 7.56 (d, J = 8.4 Hz, 2 H) | 430 |

TABLE 9-continued

| Example | R¹ | (R²)ₙ | D | A + (R³)ₘ | ¹H-NMR (300 MHz, CDCl₃) | MS |
|---|---|---|---|---|---|---|
| 71 | t-Bu | 4-CF₃ | — | 3,5-diCl-phenyl | 1.48 (s, 9 H), 6.50 (d, J = 1.7 Hz, 2 H), 6.74 (s, 1 H), 6.97 (t, J = 1.7 Hz, 1 H), 7.17 (d, J = 8.3 Hz, 2 H), 7.49 (s, 1 H), 7.57 (d, J = 8.3 Hz, 2 H) | 430 |
| 72 | t-Bu | 4-CF₃ | — | 3,4-diCl-phenyl | 1.49 (s, 9 H), 6.44 (dd, J = 2.7, 8.6 Hz, 1 H), 6.76 (d, J = 2.7 Hz, 1 H), 6.79 (s, 1 H), 7.14 (d, J = 8.8 Hz, 2 H), 7.30 (d, J = 8.6 Hz, 1 H), 7.41 (s, 1 H), 7.56 (d, J = 8.8 Hz, 2 H) | 430 |
| 73 | t-Bu | 4-Br | — | 3-F-phenyl | 1.48 (s, 9 H), 6.30-6.34 (m, 1 H), 6.38-6.42 (m, 1 H), 6.62-6.69 (m, 1 H), 6.75 (s, 1 H), 6.95 (d, J = 9.0 Hz, 2 H), 7.15-7.23 (m, 1 H), 7.38 (s, 1 H), 7.39 (d, J = 9.0 Hz, 2 H) | 390 |
| 74 | t-Bu | 4-Br | — | 4-F-phenyl | 1.48 (s, 9 H), 6.57-6.62 (m, 2 H), 6.77 (s, 1 H), 6.91 (d, J = 8.8 Hz, 2 H), 6.93-6.98 (m, 2 H), 7.21 (s, 1 H), 7.37 (d, J = 8.8 Hz, 2 H) | 390 |
| 75 | t-Bu | 4-Br | — | 4-Cl-phenyl | 1.48 (s, 9 H), 6.55 (d, J = 8.6 Hz, 2 H), 6.76 (s, 1 H), 6.93 (d, J = 9.0 Hz, 2 H), 7.20 (d, J = 8.6 Hz, 2 H), 7.24 (s, 1 H), 7.38 (d, J = 9.0 Hz, 2 H) | 408 |
| 76 | t-Bu | 4-Br | — | 4-Br-phenyl | 1.47 (s, 9 H), 6.50 (d, J = 8.7 Hz, 2 H), 6.74 (s, 1 H), 6.94 (d, J = 8.9 Hz, 2 H), 7.25 (s, 1 H), 7.35 (d, J = 8.7 Hz, 2 H), 7.39 (d, J = 8.9 Hz, 2 H) | 452 |
| 77 | t-Bu | 4-Br | — | 4-CN-phenyl | 1.47 (s, 9 H), 6.62 (d, J = 8.6 Hz, 2 H), 6.83 (s, 1 H), 6.97 (d, J = 8.6 Hz, 2 H), 7.36 (s, 1 H), 7.42 (d, J = 8.6 Hz, 2 H), 7.53 (d, J = 8.6 Hz, 2 H) | 397 |
| 78 | t-Bu | 4-Br | — | 4-ethynyl-phenyl | 1.48 (s, 9 H), 3.01 (s, 1 H), 6.55 (d, J = 8.5 Hz, 2 H), 6.82 (s, 1 H), 6.94 (d, J = 8.9 Hz, 2 H), 7.27 (s, 1 H), 7.38 (d, J = 8.5 Hz, 2 H), 7.39 (d, J = 8.9 Hz, 2 H) | 396 |

TABLE 10

| Example | R¹ | (R²)ₙ | D | A + (R³)ₘ | ¹H-NMR (300 MHz, CDCl₃) | MS |
|---|---|---|---|---|---|---|
| 79 | t-Bu | 4-Br | — | 3,5-diCl-phenyl | 1.47 (s, 9 H), 6.48 (d, J = 1.7 Hz, 2 H), 6.66 (s, 1 H), 6.94 (t, J = 1.7 Hz, 1 H), 6.99 (d, J = 8.8 Hz, 2 H), 7.40 (s, 1 H), 7.41 (d, J = 8.8 Hz, 2 H) | 442 |
| 80 | t-Bu | 4-Br | — | 3,4-diCl-phenyl | 1.47 (s, 9 H), 6.42 (dd, J = 2.6, 8.6 Hz, 1 H), 6.70 (s, 1 H), 6.73 (d, J = 2.6 Hz, 1 H), 6.97 (d, J = 8.8 Hz, 2 H), 7.28 (d, J = 8.6 Hz, 1 H), 7.31 (s, 1 H), 7.40 (d, J = 8.8 Hz, 2 H) | 442 |

TABLE 10-continued

| Example | R¹ | (R²)n | D | A + (R³)m | ¹H-NMR (300 MHz, CDCl₃) | MS |
|---|---|---|---|---|---|---|
| 81 | t-Bu | 4-CN | — | 3-F-phenyl | 1.49 (s, 9 H), 6.34-6.39 (m, 1 H), 6.42-6.45 (m, 1 H), 6.67-6.73 (m, 1 H), 6.92 (s, 1 H), 7.08 (d, J = 8.7 Hz, 2 H), 7.18-7.24 (m, 1 H), 7.46 (s, 1 H), 7.56 (d, J = 8.7 Hz, 2 H) | 337 |
| 82 | t-Bu | 4-CN | — | 4-F-phenyl | 1.49 (s, 9 H), 6.62-6.67 (m, 2 H), 6.94-7.04 (m, 5 H), 7.30 (s, 1 H), 7.54 (d, J = 8.6 Hz, 2 H) | 337 |
| 83 | t-Bu | 4-CN | — | 4-Cl-phenyl | 1.49 (s, 9 H), 6.59 (d, J = 8.6 Hz, 2 H), 6.93 (s, 1 H), 7.06 (d, J = 8.8 Hz, 2 H), 7.23 (d, J = 8.6 Hz, 2 H), 7.34 (s, 1 H), 7.55 (d, J = 8.8 Hz, 2 H) | 353 |
| 84 | t-Bu | 4-CN | — | 4-Br-phenyl | 1.49 (s, 9 H), 6.53 (d, J = 8.5 Hz, 2 H), 6.91 (s, 1 H), 7.06 (d, J = 8.8 Hz, 2 H), 7.34 (s, 1 H), 7.37 (d, J = 8.8 Hz, 2 H), 7.56 (d, J = 8.5 Hz, 2 H) | 397 |
| 85 | t-Bu | 4-CN | — | 4-CN-phenyl | 1.49 (s, 9 H), 6.65 (d, J = 8.8 Hz, 2 H), 6.99 (s, 1 H), 7.12 (d, J = 8.8 Hz, 2 H), 7.46 (s, 1 H), 7.56 (d, J = 8.8 Hz, 2 H), 7.59 (d, J = 8.8 Hz, 2 H) | 344 |
| 86 | t-Bu | 4-CN | — | 4-ethynyl-phenyl | 1.49 (s, 9 H), 3.03 (s, 1 H), 6.58 (d, J = 8.6 Hz, 2 H), 6.99 (s, 1 H), 7.06 (d, J = 8.8 Hz, 2 H), 7.36 (s, 1 H), 7.40 (d, J = 8.6 Hz, 2 H), 7.56 (d, J = 8.8 Hz, 2 H) | 343 |
| 87 | t-Bu | 4-CN | — | 4-OMe-phenyl | 1.50 (s, 9 H), 3.78 (s, 3 H), 6.68 (d, J = 8.8 Hz, 2 H), 6.83 (d, J = 8.8 Hz, 2 H), 6.96 (s, 1 H), 6.97 (d, J = 8.8 Hz, 2 H), 7.30 (s, 1 H), 7.52 (d, J = 8.8 Hz, 2 H) | 349 |
| 88 | t-Bu | 4-CN | — | 3,5-diCl-phenyl | 1.49 (s, 9 H), 6.51 (d, J = 1.7 Hz, 2 H), 6.82 (s, 1 H), 6.99 (t, J = 1.7 Hz, 1 H), 7.13 (d, J = 8.8 Hz, 2 H), 7.48 (s, 1 H), 7.59 (d, J = 8.8 Hz, 2 H) | 387 |

TABLE 11

| Example | R¹ | (R²)n | D | A + (R³)m | ¹H-NMR (300 MHz, CDCl₃) | MS |
|---|---|---|---|---|---|---|
| 89 | t-Bu | 4-CN | — | 3,4-diCl-phenyl | 1.49 (s, 9 H), 6.45 (dd, J = 2.7, 8.6 Hz, 1 H), 6.77 (d, J = 2.7 Hz, 1 H), 6.87 (s, 1 H), 7.10 (d, J = 8.8 Hz, 2 H), 7.31 (d, J = 8.6 Hz, 1 H), 7.40 (s, 1 H), 7.58 (d, J = 8.8 Hz, 2 H) | 387 |

TABLE 11-continued

| Example | R¹ | (R²)ₙ | D | A + (R³)ₘ | ¹H-NMR (300 MHz, CDCl₃) | MS |
|---|---|---|---|---|---|---|
| 90 | t-Bu | 4-MeO | — | 4-Cl-phenyl (methyl) | 1.48 (s, 9 H), 3.79 (s, 3 H), 6.54 (d, J = 8.7 Hz, 2 H), 6.64 (s, 1 H), 6.86 (d, J = 9.0 Hz, 2 H), 7.02 (d, J = 9.0 Hz, 2 H), 7.19 (d, J = 8.7 Hz, 2 H), 7.29 (s, 1 H) | 358 |
| 91 | t-Bu | 4-Ac | — | 3-F-phenyl (methyl) | 1.50 (s, 9 H), 2.55 (s, 3 H), 6.34-6.39 (m, 1 H), 6.42-6.45 (m, 1 H), 6.65-6.72 (m, 1 H), 6.86 (s, 1 H), 7.09 (d, J = 8.7 Hz, 2 H), 7.14-7.26 (m, 1 H), 7.53 (s, 1 H), 7.93 (d, J = 8.7 Hz, 2 H) | 354 |
| 92 | t-Bu | 4-Ac | — | 4-F-phenyl (methyl) | 1.50 (s, 9 H), 2.54 (s, 3 H), 6.62-6.67 (m, 2 H), 6.89 (s, 1 H), 6.95-7.00 (m, 2 H), 7.04 (d, J = 8.6 Hz, 2 H), 7.37 (s, 1 H), 7.92 (d, J = 8.6 Hz, 2 H) | 354 |
| 93 | t-Bu | 4-Ac | — | 4-Cl-phenyl (methyl) | 1.50 (s, 9 H), 2.55 (s, 3 H), 6.59 (d, J = 8.6 Hz, 2 H), 6.87 (s, 1 H), 7.07 (d, J = 8.7 Hz, 2 H), 7.22 (d, J = 8.6 Hz, 2 H), 7.40 (s, 1 H), 7.93 (d, J = 8.7 Hz, 2 H) | 370 |
| 94 | t-Bu | 4-Ac | — | 4-Br-phenyl (methyl) | 1.50 (s, 9 H), 2.55 (s, 3 H), 6.53 (d, J = 8.6 Hz, 2 H), 6.85 (s, 1 H), 7.07 (d, J = 8.7 Hz, 2 H), 7.37 (d, J = 8.6 Hz, 2 H), 7.41 (s, 1 H), 7.93 (d, J = 8.7 Hz, 2 H) | 414 |
| 95 | t-Bu | 4-Ac | — | 4-ethynyl-phenyl (methyl) | 1.50 (s, 9 H), 2.55 (s, 3 H), 3.02 (s, 1 H), 6.58 (d, J = 8.6 Hz, 2 H), 6.93 (s, 1 H), 7.07 (d, J = 8.7 Hz, 2 H), 7.40 (d, J = 8.6 Hz, 2 H), 7.42 (s, 1 H), 7.93 (d, J = 8.7 Hz, 2 H) | 360 |
| 96 | t-Bu | 4-Ac | — | 4-OMe-phenyl (methyl) | 1.51 (s, 9 H), 2.54 (s, 3 H), 3.77 (s, 3 H), 6.68 (d, J = 8.9 Hz, 2 H), 6.83 (d, J = 8.9 Hz, 2 H), 6.91 (s, 1 H), 6.99 (d, J = 8.8 Hz, 2 H), 7.37 (s, 1 H), 7.89 (d, J = 8.8 Hz, 2 H) | 366 |
| 97 | t-Bu | 4-SO₂Me | — | 3-F-phenyl (methyl) | 1.50 (s, 9 H), 3.03 (s, 3 H), 6.34-6.39 (m, 1 H), 6.43-6.46 (m, 1 H), 6.67-6.73 (m, 1 H), 6.93 (s, 1 H), 7.04 (d, J = 8.8 Hz, 2 H), 7.19-7.26 (m, 1 H), 7.51 (s, 1 H), 7.85 (d, J = 8.8 Hz, 2 H) | 390 |

TABLE 12

| Example | R¹ | (R²)ₙ | D | A + (R³)ₘ | ¹H-NMR (300 MHz, CDCl₃) | MS |
|---|---|---|---|---|---|---|
| 98 | t-Bu | 4-SO₂Me | — | 4-F-phenyl (methyl) | 1.50 (s, 9 H), 3.02 (s, 3 H), 6.65 (dd, J = 8.6, 8.6 Hz, 2 H), 6.97 (d, J = 8.6 Hz, 2 H), 7.01 (s, 1 H), 7.10 (d, J = 8.7 Hz, 2 H), 7.35 (s, 1 H), 7.83 (d, J = 8.7 Hz, 2 H) | 390 |
| 99 | t-Bu | 4-SO₂Me | — | 4-Cl-phenyl (methyl) | 1.50 (s, 9 H), 3.03 (s, 3 H), 6.60 (d, J = 8.6 Hz, 2 H), 6.94 (s, 1 H), 7.14 (d, J = 8.7 Hz, 2 H), 7.24 (d, J = 8.6 Hz, 2 H), 7.39 (s, 1 H), 7.84 (d, J = 8.7 Hz, 2 H) | 406 |

TABLE 12-continued

| Example | R¹ | (R²)ₙ | D | A + (R³)ₘ | ¹H-NMR (300 MHz, CDCl₃) | MS |
|---|---|---|---|---|---|---|
| 100 | t-Bu | 4-SO₂Me | — | 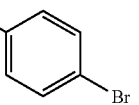 | 1.49 (s, 9 H), 3.03 (s, 3 H), 6.54 (d, J = 8.7 Hz, 2 H), 6.93 (s, 1 H), 7.14 (d, J = 8.8 Hz, 2 H), 7.37 (d, J = 8.7 Hz, 2 H), 7.40 (s, 1 H), 7.85 (d, J = 8.8 Hz, 2 H) | 450 |
| 101 | t-Bu | 4-SO₂Me | — | 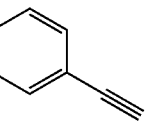 | 1.50 (s, 9 H), 3.03 (s, 3 H), 3.03 (s, 1 H), 6.59 (d, J = 8.5 Hz, 2 H), 7.00 (s, 1 H), 7.14 (d, J = 8.7 Hz, 2 H), 7.40 (d, J = 8.5 Hz, 2 H), 7.41 (s, 1 H), 7.84 (d, J = 8.7 Hz, 2 H) | 396 |
| 102 | t-Bu | 4-SO₂Me | — | 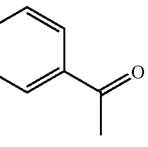 | 1.50 (s, 9 H), 2.54 (s, 3 H), 3.03 (s, 3 H), 6.66 (d, J = 8.6 Hz, 2 H), 7.05 (s, 1 H), 7.17 (d, J = 8.6 Hz, 2 H), 7.51 (s, 1 H), 7.86 (d, J = 8.6 Hz, 2 H), 7.90 (d, J = 8.6 Hz, 2 H) | 414 |
| 103 | t-Bu | 4-SO₂Me | — | 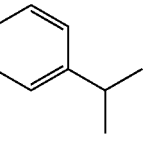 | 1.22 (d, J = 7.0 Hz, 6 H), 1.50 (s, 9 H), 2.86 (sep, J = 7.0 Hz, 1 H), 3.02 (s, 3 H), 6.63 (d, J = 8.4 Hz, 2 H), 6.96 (s, 1 H), 7.10 (d, J = 8.8 Hz, 2 H), 7.13 (d, J = 8.4 Hz, 2 H), 7.45 (s, 1 H), 7.82 (d, J = 8.8 Hz, 2 H) | 414 |
| 104 | t-Bu | 3,4-Cl | — | 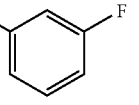 | 1.48 (s, 9 H), 6.30-6.35 (m, 1 H), 6.39-6.42 (m, 1 H), 6.45-6.71 (m, 1 H), 6.81 (s, 1 H), 6.89 (dd, J = 2.6, 8.6 Hz, 1 H), 7.16 (d, J = 2.6 Hz, 1 H), 7.17-7.24 (m, 1 H), 7.31 (s, 1 H), 7.33 (d, J = 8.6 Hz, 1 H) | 380 |
| 105 | t-Bu | 4-Br | — | 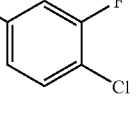 | 1.47 (s, 9 H), 6.35-6.42 (m, 2 H), 6.72 (s, 1 H), 6.97 (d, J = 8.9 Hz, 2 H), 7.21-7.27 (m, 1 H), 7.34 (s, 1 H), 7.41 (d, J = 8.9 Hz, 2 H) | 424 |
| 106 | t-Bu | 4-ethynyl | — | 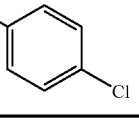 | 1.48 (s, 9 H), 3.03 (s, 1 H), 6.56 (d, J = 8.6 Hz, 2 H), 6.78 (s, 1 H), 6.99 (d, J = 8.8 Hz, 2 H), 7.21 (d, J = 8.8 Hz, 2 H), 7.31 (s, 1 H), 7.42 (d, J = 8.6 Hz, 2 H) | 352 |

TABLE 13

| Example | R¹ | R² | D | A + R³ | ¹H-NMR (300 MHz, CDCl₃) | MS |
|---|---|---|---|---|---|---|
| 107 | t-Bu | 3,4-Cl | — | 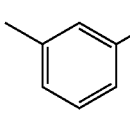 | 1.48 (s, 9 H), 3.05 (s, 1 H), 6.54-6.57 (m, 1 H), 6.78 (s, 1 H), 6.81 (s, 1 H), 6.87 (dd, J = 2.7, 8.7 Hz, 1 H), 7.10-7.12 (m, 1 H), 7.13 (d, J = 2.7 Hz, 1 H), 7.15 (s, 1 H), 7.16-7.24 (m, 1 H), 7.32 (d, J = 8.7 Hz, 1 H) | 386 |
| 108 | t-Bu | 4-ethynyl | — | 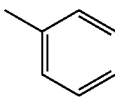 | 1.49 (s, 9 H), 3.03 (s, 1 H), 6.46 (dd, J = 2.2, 8.1 Hz, 1 H), 6.67 (dd, J = 2.0, 2.2 Hz, 1 H), 6.75 (s, 1 H), 6.93-6.96 (m, 1 H), 7.01 (d, J = 8.6 Hz, 2 H), 7.17 (dd, J = 7.9, 8.1 Hz, 1 H), 7.40 (s, 1 H), 7.43 (d, J = 8.6 Hz, 2 H) | 352 |

TABLE 13-continued

| Example | R¹ | R² | D | A + R³ | ¹H-NMR (300 MHz, CDCl₃) | MS |
|---|---|---|---|---|---|---|
| 109 | n-Bu | 4-Cl | — | 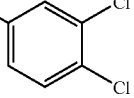 | 0.97 (t, J = 7.3 Hz, 3 H), 1.41 (qt, J = 7.3, 7.5 Hz, 2 H), 1.70 (tt, J = 7.5, 7.5 Hz, 2 H), 3.02 (t, J = 7.5 Hz, 2 H), 6.43 (d, J = 8.6 Hz, 1 H), 6.73 (s, 1 H), 6.74 (s, 1 H), 7.05 (d, J = 8.8 Hz, 2 H), 7.25-7.31 (m, 2 H), 7.30 (d, J = 8.6 Hz, 1 H) | 396 |
| 110 | 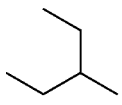 | 4-Cl | — | 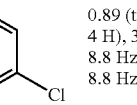 | 0.89 (t, J = 7.4 Hz, 3 H), 1.52-1.82 (m, 4 H), 3.65-3.74 (m, 1 H), 6.56 (d, J = 8.8 Hz, 2 H), 6.84 (s, 1 H), 7.02 (d, J = 8.8 Hz, 2 H), 7.21-7.27 (m, 5 H) | 376 |
| 111 | n-Bu | 4-Cl | — | 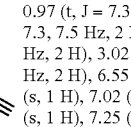 | 0.97 (t, J = 7.3 Hz, 3 H), 1.42 (qt, J = 7.3, 7.5 Hz, 2 H), 1.71 (tt, J = 7.5, 7.5 Hz, 2 H), 3.02 (s, 1 H), 3.03 (t, J = 7.5 Hz, 2 H), 6.55 (d, J = 8.5 Hz, 2 H), 6.85 (s, 1 H), 7.02 (d, J = 8.8 Hz, 2 H), 7.21 (s, 1 H), 7.25 (d, J = 8.8 Hz, 2 H), 7.40 (d, J = 8.5 Hz, 2 H) | 352 |
| 112 | 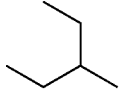 | 4-Cl | — | 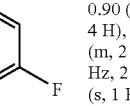 | 0.90 (t, J = 7.4 Hz, 3 H), 1.51-1.82 (m, 4 H), 3.66-3.75 (m, 1 H), 6.60-6.64 (m, 2 H), 6.85 (s, 1 H), 6.96 (d, J = 9.6 Hz, 2 H), 6.99 (d, J = 9.0 Hz, 2 H), 7.20 (s, 1 H), 7.24 (d, J = 9.6 Hz, 2 H) | 360 |
| 113 | 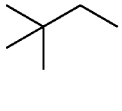 | 4-Cl | — | 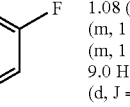 | 1.08 (s, 9 H), 2.95 (s, 2 H), 6.31-6.36 (m, 1 H), 6.39-6.42 (m, 1 H), 6.65-6.71 (m, 1 H), 6.86 (s, 1 H), 7.03 (d, J = 9.0 Hz, 2 H), 7.17-7.25 (m, 1 H), 7.26 (d, J = 9.0 Hz, 2 H), 7.30 (s, 1 H) | 360 |

TABLE 14

| Example | R¹ | R² | D | A + R³ | ¹H-NMR (300 MHz, CDCl₃) | MS |
|---|---|---|---|---|---|---|
| 114 | 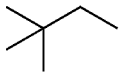 | 4-Cl | — | 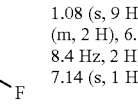 | 1.08 (s, 9 H), 2.95 (s, 2 H), 6 59-6.63 (m, 2 H), 6.88 (s, 1 H), 6.95 (d, J = 8.4 Hz, 2 H), 6.98 (d, J = 8.8 Hz, 2 H), 7.14 (s, 1 H), 7.24 (d, J = 8.8 Hz, 2 H) | 360 |
| 115 | n-Bu | 4-Cl | — | 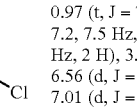 | 0.97 (t, J = 7.2 Hz, 3 H), 1.42 (qt, J = 7.2, 7.5 Hz, 2 H), 1.70 (tt, J = 7.5, 7.5 Hz, 2 H), 3.03 (t, J = 7.5 Hz, 2 H), 6.56 (d, J = 8.8 Hz, 2 H), 6.79 (s, 1 H), 7.01 (d, J = 8.8 Hz, 2 H), 7.17 (s, 1 H), 7.20-7.26 (m, 4 H) | 362 |
| 116 | 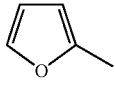 | 4-Cl | — | 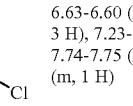 | 6.63-6.60 (m, 3 H), 6.99-7.02 (m, 3 H), 7.23-7.29 (m, 4 H), 7.38 (s, 1 H), 7.74-7.75 (m, 1 H), 7.84-7.85 (m, 1 H) | 372 |
| 117 | 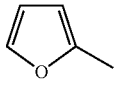 | 4-Cl | — | 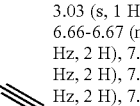 | 3.03 (s, 1 H), 6.64 (d, J = 8.8 Hz, 2 H), 6.66-6.67 (m, 1 H), 7.01 (d, J = 9.0 Hz, 2 H), 7.06 (s, 1 H), 7.28 (d, J = 9.0 Hz, 2 H), 7.40 (s, 1 H), 7.41 (d, J = 8.8 Hz, 2 H), 7.74-7.75 (m, 1 H), 7.83-7.84 (m, 1 H) | 362 |
| 118 | 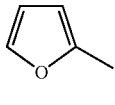 | 4-Cl | — | 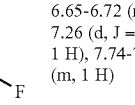 | 6.65-6.72 (m, 3 H), 6.96-7.02 (m, 5 H), 7.26 (d, J = 8.8 Hz, 2 H), 7.34 (s, 1 H), 7.74-7.75 (m, 1 H), 7.84-7.85 (m, 1 H) | 356 |
| 119 | 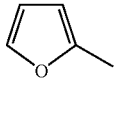 | 4-Cl | — | 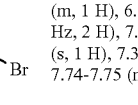 | 6.59 (d, J = 8.8 Hz, 2 H), 6.65-6.67 (m, 1 H), 6.99 (s, 1 H), 7.02 (d, J = 9.0 Hz, 2 H), 7.28 (d, J = 9.0 Hz, 2 H), 7.37 (s, 1 H), 7.38 (d, J = 8.8 Hz, 2 H), 7.74-7.75 (m, 1 H), 7.83-7.85 (m, 1 H) | 416 |

TABLE 14-continued

| Example | R¹ | R² | D | A + R³ | ¹H-NMR (300 MHz, CDCl₃) | MS |
|---|---|---|---|---|---|---|
| 120 | 2-furyl | 4-Cl | — | 3-CF₃-phenyl | 6.66-6.68 (m, 1 H), 6.81 (d, J = 8.2 Hz, 1 H), 6.97 (s, 1 H), 7.03 (d, J = 8.8 Hz, 2 H), 7.11 (s, 1 H), 7.24-7.30 (m, 3 H), 7.36-7.41 (m, 2 H), 7.75-7.76 (m, 1 H), 7.86-7.87 (m, 1 H) | 406 |
| 121 | ClCH₂C(CH₃)₂– | 4-Cl | — | 3-CF₃-phenyl | 1.54 (s, 6 H), 4.16 (s, 2 H), 6.74 (d, J = 8.6 Hz, 1 H), 6.80 (s, 2 H), 6.96-6.99 (m, 3 H), 7.22-7.28 (m, 3 H), 7.34-7.39 (m, 2 H) | 412 |
| 122 | ClCH₂C(CH₃)₂– | 4-Cl | — | 4-ethynyl-phenyl | 1.54 (s, 6 H), 3.02 (s, 1 H), 4.15 (s, 2 H), 6.58 (d, J = 8.4 Hz, 2 H), 6.80 (s, 1 H), 6.95 (d, J = 8.6 Hz, 2 H), 7.26 (d, J = 8.6 Hz, 2 H), 7.30 (s, 1 H), 7.39 (d, J = 8.4 Hz, 2 H) | 368 |

TABLE 15

| Example | R¹ | R² | D | A + R³ | ¹H-NMR (300 MHz, CDCl₃) | MS |
|---|---|---|---|---|---|---|
| 123 | t-Bu | 3,4-Cl | — | 3-Cl-phenyl | 1.48 (s, 9 H), 6.45 (dd, J = 2.0, 8.1 Hz, 1 H), 6.65 (dd, J = 1.7, 2.0 Hz, 1 H), 6.79 (s, 1 H), 6.89 (dd, J = 2.6, 8.7 Hz, 1 H), 6.96 (dd, J = 1.7, 7.6 Hz, 1 H), 7.17 (d, J = 2.6 Hz, 2 H), 7.17 (dd, J = 7.6, 8.1 Hz, 1 H), 7.26 (s, 1 H), 7.33 (d, J = 8.7 Hz, 1 H) | 396 |
| 124 | t-Bu | 3,4-Cl | — | 4-Cl-phenyl | 1.48 (s, 9 H), 6.55 (d, J = 8.8 Hz, 2 H), 6.82 (s, 1 H), 6.86 (dd, J = 2.6, 8.7 Hz, 1 H), 7.15 (d, J = 2.6 Hz, 1 H), 7.18 (s, 1 H), 7.22 (d, J = 8.8 Hz, 2 H), 7.32 (d, J = 8.7 Hz, 1 H) | 396 |
| 125 | 2-thienyl | 4-Cl | — | 4-Cl-phenyl | 6.66 (d, J = 9.0 Hz, 2 H), 7.04 (s, 1 H), 7.11 (d, J = 9.0 Hz, 2 H), 7.18-7.21 (m, 1 H), 7.23-7.30 (m, 3 H), 7.36 (s, 1 H), 7.76 (d, J = 5.1 Hz, 1 H), 8.24 (dd, J = 0.9, 3.9 Hz, 1 H) | 388 |
| 126 | t-Bu | 4-Cl | — | isoquinolin-5-yl | 1.54 (s, 9 H), 6.43 (d, J = 8.1 Hz, 1 H), 7.00 (d, J = 8.1 Hz, 2 H), 7.23 (d, J = 8.1 Hz, 2 H), 7.33 (s, 1 H), 7.37 (s, 1 H), 7.45 (t, J = 8.1 Hz, 1 H), 7.60 (d, J = 8.1 Hz, 1 H), 8.29 (d, J = 6.0 Hz, 1 H), 8.56 (d, J = 6.0 Hz, 1 H), 9.21 (s, 1 H) | 379 |
| 127 | t-Bu | 4-Cl | — | quinolin-8-yl | 1.49 (s, 9 H), 6.32 (dd, J = 1.8, 6.9 Hz, 1 H) 7.04 (d, J = 9.0 Hz, 2 H) 7.24 (d, J = 9.0 Hz, 2 H), 7.30-7.33 (m, 2 H), 7.42 (dd, J = 4.2, 8.4 Hz, 1 H), 7.81 (s, 1 H), 8.10 (dd, J = 1.8, 8.4 Hz, 1 H), 8.49 (s, 1 H), 8.84 (dd, J = 1.8, 4.2 Hz, 1 H) | 379 |
| 128 | t-Bu | 4-Cl | — | pyridin-3-yl | 1.48 (s, 9 H), 6.76 (d, J = 2.7 Hz, 2 H), 6.78 (s, 1 H), 7.01 (d, J = 9.0 Hz, 2 H), 7.15-7.27 (m, 3 H), 7.35 (s, 1 H), 8.16 (d, J = 2.7 Hz, 1 H), 8.21 (dd, J = 1.2, 4.8 Hz, 1 H) | 329 |
| 129 | t-Bu | 4-Cl | — | 5-Cl-pyridin-2-yl | 1.65 (s, 9 H), 7.43 (dd, J = 2.0, 9.4 Hz, 2 H), 7.47 (d, J = 8.6 Hz, 2 H), 7.67 (d, J = 9.4 Hz, 1 H), 7.79 (d, J = 8.6 Hz, 2 H), 10.02 (d, J = 2.0 Hz, 1 H) | 363 |

TABLE 15-continued

| Example | R¹ | R² | D | A + R³ | ¹H-NMR (300 MHz, CDCl₃) | MS |
|---|---|---|---|---|---|---|
| 130 | F₃C-C₆H₄- | 4-Cl | — | 4-Cl-C₆H₄- | 6.66 (d, J = 8.7 Hz, 1 H), 6.91 (d, J = 8.7 Hz, 1 H), 6.98 (s, 1 H), 7.24 (d, J = 8.7 Hz, 1 H), 7.26 (d, J = 8.7 Hz, 1 H), 7.52 (s, 1 H), 7.77 (d, J = 8.7 Hz, 1 H), 8.22 (d, J = 8.7 Hz, 1 H) | 450 |

TABLE 16

| Example | R¹ | R² | D | A + R³ | ¹H-NMR (300 MHz, CDCl₃) | MS |
|---|---|---|---|---|---|---|
| 131 | t-Bu | 4-ethynyl | — | 3-F-C₆H₄- | 1.49 (s, 9 H), 3.03 (s, 1 H), 6.32-6.37 (m, 1 H), 6.40-6.43 (m, 1 H), 6.63-6.70 (m, 1 H), 6.78 (s, 1 H), 7.01 (d, J = 8.6 Hz, 2 H), 7.16-7.24 (m, 1 H), 7.42 (d, J = 8.6 Hz, 2 H), 7.44 (s, 1 H) | 336 |
| 132 | t-Bu | 3,4-Cl | — | 4-ethynyl-C₆H₄- | 1.48 (s, 9 H), 3.02 (s, 1 H), 6.55 (d, J = 8.6 Hz, 2 H), 6.87 (dd, J = 2.6, 8.8 Hz, 1 H), 6.88 (s, 1 H), 7.16 (d, J = 2.6 Hz, 1 H), 7.20 (s, 1 H), 7.32 (d, J = 8.8 Hz, 1 H), 7.39 (d, J = 8.6 Hz, 2 H) | 386 |
| 133 | t-Bu | 4-Cl | — | 3-Cl-C₆H₄- | 1.48 (s, 9 H), 6.45 (dd, J = 2.0, 8.0 Hz, 1 H), 6.65 (t, J = 2.0 Hz, 1 H), 6.72 (s, 1 H), 6.93 (d, J = 8.2 Hz, 1 H), 7.01 (d, J = 8.7 Hz, 2 H), 7.16 (dd, J = 8.0, 8.2 Hz, 1 H), 7.25 (d, J = 8.7 Hz, 2 H), 7.33 (s, 1 H) | 362 |
| 134 | t-Bu | 4-Cl | — | 4-Br-C₆H₄- | 1.47 (s, 9 H), 6.50 (d, J = 8.7 Hz, 2 H), 6.73 (s, 1 H), 6.99 (d, J = 8.7 Hz, 2 H), 7.24 (d, J = 8.7 Hz, 2 H), 7.26 (s, 1 H), 7.34 (d, J = 8.7 Hz, 2 H) | 406 |
| 135 | t-Bu | 4-Cl | — | 3-F-4-Cl-C₆H₃- | 1.47 (s, 9 H), 6.35-6.42 (m, 2 H), 6.72 (s, 1 H), 7.02 (d, J = 8.7 Hz, 2 H), 7.21-7.29 (m, 1 H), 7.26 (d, J = 8.7 Hz, 2 H), 7.36 (s, 1 H) | 380 |
| 136 | t-Bu | 4-Cl | — | 4-ethynyl-C₆H₄- | 1.48 (s, 9 H), 3.01 (s, 1 H), 6.55 (d, J = 8.5 Hz, 2 H), 6.81 (s, 1 H), 6.99 (d, J = 8.8 Hz, 2 H), 7.24 (d, J = 8.8 Hz, 2 H), 7.26 (s, 1 H), 7.38 (d, J = 8.5 Hz, 2 H) | 352 |
| 137 | sec-pentyl (CH(Et)(CH₂CH(CH₃))) | 4-Cl | — | 3-Cl-C₆H₄- | 0.90 (t, J = 7.4 Hz, 3 H), 1.52-1.82 (m, 4 H), 3.64-3.73 (m, 1 H), 6.46 (dd, J = 2.0, 8.1 Hz, 1 H), 6.67 (dd, J = 2.0, 2.0 Hz, 1 H), 6.81 (s, 1 H), 6.94-6.97 (m, 1 H), 7.04 (d, J = 8.8 Hz, 2 H), 7.18 (dd, J = 7.9, 8.1 Hz, 1 H), 7.26 (d, J = 8.8 Hz, 2 H), 7.32 (s, 1 H) | 376 |
| 138 | t-Bu | 4-ethynyl | — | 4-ethynyl-C₆H₄- | 1.49 (s, 9 H), 3.02 (s, 1 H), 3.04 (s, 1 H), 6.56 (d, J = 8.7 Hz, 2 H), 6.85 (s, 1 H), 7.00 (d, J = 8.7 Hz, 2 H), 7.33 (s, 1 H), 7.39 (d, J = 8.7 Hz, 2 H), 7.42 (d, J = 8.7 Hz, 2 H) | 342 |
| 139 | neopentyl (CH₂C(CH₃)₃) | 4-Cl | — | 4-Cl-C₆H₄- | 1.08 (s, 9 H), 2.95 (s, 2 H), 6.56 (d, J = 8.6 Hz, 2 H), 6.87 (s, 1 H), 7.01 (d, J = 8.8 Hz, 2 H), 7.17 (s, 1 H), 7.21-7.27 (m, 4 H) | 376 |

TABLE 17

| Example | R¹ | R² | D | A + R³ | $^1$H-NMR (300 MHz, CDCl$_3$) | MS |
|---|---|---|---|---|---|---|
| 140 | t-Bu | 4-Cl | — | 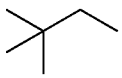Cl | 1.08 (s, 9 H), 2.95 (s, 2 H), 6.45 (dd, J = 2.1, 8.1 Hz, 1 H), 6.66 (dd, J = 2.1, 2.1 Hz, 1 H), 6.84 (s, 1 H), 6.94-6.97 (m, 1 H), 7.03 (d, J = 8.8 Hz, 2 H), 7.17 (dd, J = 7.9, 8.1 Hz, 1 H), 7.26 (d, J = 8.8 Hz, 2 H), 7.28 (s, 1 H) | 376 |
| 141 | n-Bu | 4-Cl | — | 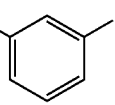Cl | 0.97 (t, J = 7.2 Hz, 3 H), 1.42 (qt, J = 7.2, 7.5 Hz, 2 H), 1.71 (tt, J = 7.5, 7.5 Hz, 2 H), 3.03 (t, J = 7.5 Hz, 2 H), 6.47 (ddd, J = 2.2, 2.2, 8.1 Hz, 1 H), 6.65 (dd, J = 2.0, 2.2 Hz, 1 H), 6.76 (s, 1 H), 6.95 (ddd, J = 2.2, 2.2, 8.1 Hz, 1 H), 7.03 (d, J = 8.8 Hz, 2 H), 7.17 (dd, J = 8.1, 8.1 Hz, 1 H), 7.25 (d, J = 8.8 Hz, 2 H), 7.27 (s, 1 H) | 362 |

The representative compounds of the present invention were tested for the antagonistic action against S1P$_3$ receptors as in the following Test Examples.

Test Example 1

Suppressive Effect on the Increase in the Calcium Ion Concentration in Cells ($[Ca^{2+}]_i$)

The changes in $[Ca^{2+}]_i$ caused by S1P stimuli were measured by the following method.

CHO-K1 cells expressing an S1P$_3$ receptor subtype were suspended in Nutrient mixture F-12 HAM (HAM, SIGMA) containing 10% (v/v) fetal bovine serum (FBS, SIGMA), and the suspension was inoculated on a 96-well plate, and then cultured for 24 hours. The culture solution was removed, the cells were washed once with HAM containing 1% FBS, and then the cells were cultured for another 24 hours using the same culture solution. The culture solution was removed again, and the cells were washed once with an HBSS (+) buffer solution. The same buffer solution which was prepared to have a fluorescent Ca$^{2+}$ indicator Fura 2-AM (Molecular Probe, Inc.) at a concentration of 5 µmol/L, was added, and the cells were incubated for 60 minutes at 37° C. The cells were washed once with Hanks' buffer solution containing 20 mM HEPES (hereinafter, referred to as HBSS (+) buffer solution), and 200 µL of a test compound solution was added. Then, the cells were incubated for 20 minutes at 37° C. The plate was placed in a fluorescence measuring apparatus (Flex-Station II, Molecular Devices, Inc.) to measure the baseline, then 50 µL of an S1P solution (50 nmol/L) was added thereto, and an increase in $[Ca^{2+}]_i$ caused by the S1P solution was measured for 30 seconds at an interval of 3.33 seconds (excited at 335 nm and 362 nm, detected at 505 nm and 512 nm).

The selectivity to the S1P receptor subtype was examined in the following manner. First, CHO-K1 cells which stably express each of the receptor subtypes S1P$_1$, S1P$_2$ and S1P$_3$ were suspended in HAM containing 10% (v/v) FBS, the suspension was inoculated on a 96-well plate, and then the cells were cultured for 24 hours. The culture solution was removed, the cells were washed once with HAM containing 1% FBS, and the cells were cultured for another 24 hours using 50 µL of the same culture solution. Furthermore, a Calcium3 (Molecular Devices, Inc.) solution prepared in HBSS (+) buffer, which is a fluorescent Ca$^{2+}$ indicator, was added, and the cells were incubated for 60 minutes at 37° C. Then, 100 µL of a test compound solution prepared to a concentration of 2×10 µmol/L was added, and the cells were incubated for 20 minutes at 37° C. The plate was placed in a fluorescence measuring apparatus (Flex Station II, Molecular Devices, Inc.) to measure the baseline, then 50 µL of an S1P solution (50 nmol/L for S1P3 receptor, and 100 nmol/L for other receptors) was added thereto, and an increase in $[Ca^{2+}]_i$ caused by the S1P solution was measured for 30 seconds at an interval of 2 seconds (excited at 485 nm, detected at 525 nm). The indicator was prepared and used according to the instruction manual.

A solution of the test compound was prepared by dissolving each of the test compounds in DMSO to a concentration of 10 mmol/L, and then diluting the solution with an HBSS (+) buffer solution to the predetermined concentration. For the control, an HBSS (+) buffer solution containing 0.1% DMSO was used instead of the test compound solution, and an HBSS (+) buffer solution containing 0.025% DMSO was used in place of the S1P solution for blank test. The measurement values were obtained by subtracting the maximum RFU value for the blind test from the maximum RFU values for control or each test compounds. A decrease in the measurement value for the test compound relative to the control was indicated as the suppression rate (%), from which the IC$_{50}$ value was calculated. These test results are presented in Tables 18 and 19.

TABLE 18

| Compound No. | hS1P$_3$ suppression IC$_{50}$ (µM) |
|---|---|
| 1 | 6.72 |
| 3 | 14.69 |
| 4 | 2.81 |
| 9 | 4.57 |
| 11 | 5.34 |
| 12 | 4.84 |
| 13 | 3.12 |
| 14 | 1.87 |
| 16 | 3.94 |
| 17 | 1.92 |
| 18 | 2.34 |
| 19 | 3.64 |
| 20 | 2.18 |
| 21 | 26.77 |
| 23 | 14.52 |
| 25 | 11.72 |
| 28 | 7.97 |
| 29 | 5.11 |
| 30 | 12.33 |
| 31 | 10.47 |
| 32 | 1.71 |
| 33 | 0.47 |
| 34 | 1.22 |

TABLE 18-continued

| Compound No. | hS1P$_3$ suppression IC$_{50}$ (μM) |
|---|---|
| 35 | 7.49 |
| 36 | 2.53 |
| 37 | 0.49 |
| 38 | 0.31 |
| 41 | 3.54 |
| 42 | 2.89 |
| 49 | 5.32 |
| 50 | 3.74 |
| 51 | 2.44 |
| 52 | 1.02 |
| 53 | 4.47 |
| 54 | 4.38 |
| 55 | 2.75 |
| 56 | 2.16 |
| 57 | 4.95 |
| 58 | 5.72 |
| 59 | 1.39 |
| 60 | 1.02 |
| 61 | 3.22 |
| 62 | 1.72 |
| 63 | 5.71 |
| 65 | 0.67 |
| 66 | 7.05 |
| 67 | 8.20 |
| 68 | 9.09 |
| 72 | 3.64 |
| 73 | 1.90 |
| 74 | 2.32 |
| 75 | 1.17 |
| 76 | 1.66 |
| 77 | 1.51 |
| 78 | 0.97 |
| 80 | 0.38 |
| 81 | 5.52 |
| 82 | 5.07 |
| 86 | 6.64 |
| 87 | 14.03 |
| 90 | 6.58 |
| 91 | 8.90 |
| 92 | 11.57 |
| 95 | 18.58 |
| 99 | 10.57 |
| 104 | 0.43 |
| 105 | 0.52 |
| 106 | 0.66 |
| 107 | 0.69 |
| 108 | 0.84 |
| 109 | 0.76 |
| 110 | 0.97 |
| 111 | 1.55 |
| 112 | 1.66 |
| 113 | 1.78 |
| 114 | 2.09 |
| 115 | 2.47 |
| 116 | 2.07 |
| 117 | 2.34 |
| 118 | 3.85 |
| 119 | 4.23 |
| 120 | 5.45 |
| 121 | 2.32 |
| 122 | 3.86 |
| 123 | 0.34 |
| 124 | 0.45 |
| 125 | 8.29 |
| 131 | 0.75 |
| 132 | 0.82 |
| 133 | 0.84 |
| 134 | 0.87 |
| 135 | 0.90 |
| 136 | 0.99 |
| 137 | 1.59 |
| 138 | 1.62 |
| 139 | 1.70 |
| 140 | 1.99 |
| 141 | 1.99 |

TABLE 19

| Compound No. | Suppression rate at 10 μM (%) | | |
|---|---|---|---|
| | hS1P$_3$ | hS1P$_1$ | hS1P$_2$ |
| 3 | 68.5 | 18.6 | −0.4 |
| 13 | 99.0 | 26.1 | −16.7 |
| 19 | 101.4 | −25.4 | −8.6 |
| 20 | 66.5 | −3.5 | −4.6 |
| 21 | 91.1 | 17.5 | 13.7 |
| 28 | 79.0 | 14.6 | 14.2 |
| 29 | 90.4 | 29.7 | 17.4 |
| 32 | 100.1 | 22.4 | −11.1 |
| 33 | 97.5 | 29.5 | 1.7 |
| 41 | 103.4 | 18.4 | 27.1 |
| 42 | 93.8 | 7.9 | 32.9 |
| 49 | 96.6 | 6.6 | 3.6 |
| 50 | 97.7 | 25.1 | 13.6 |
| 52 | 100.8 | 29.5 | 26.2 |
| 53 | 100.4 | 27.1 | 18.5 |
| 54 | 101.0 | 22.0 | 16.0 |
| 57 | 73.9 | 11.5 | 15.0 |
| 61 | 95.5 | −2.9 | 8.1 |
| 62 | 95.5 | −9.7 | 7.4 |
| 63 | 76.5 | −9.1 | −1.4 |
| 64 | 94.6 | −1.0 | 9.1 |
| 65 | 96.3 | 5.1 | 10.0 |
| 67 | 90.2 | 20.8 | 15.5 |
| 73 | 100.1 | 5.1 | 22.3 |
| 74 | 104.7 | 20.4 | 23.2 |
| 75 | 101.8 | 17.0 | 17.9 |
| 76 | 103.0 | 5.1 | 26.1 |
| 78 | 105.4 | 25.1 | 20.8 |
| 80 | 101.3 | 20.6 | 26.3 |
| 104 | 95.9 | 28.3 | 18.9 |
| 108 | 88.9 | 11.1 | 15.8 |
| 111 | 95.1 | −16.6 | 23.1 |
| 112 | 86.6 | 22.1 | 12.8 |
| 113 | 92.5 | 5.9 | 20.7 |
| 115 | 101.8 | 24.3 | 27.0 |
| 117 | 98.6 | 20.4 | 31.6 |
| 122 | 89.9 | 4.9 | 7.1 |
| 131 | 81.7 | 15.7 | 24.7 |
| 133 | 91.7 | 16.7 | 37.7 |
| 134 | 96.5 | 36.4 | 29.8 |
| 136 | 94.3 | 40.3 | 33.7 |
| 137 | 86.0 | 35.3 | 30.1 |
| 138 | 79.9 | 14.1 | 8.0 |
| 139 | 82.3 | 14.9 | 40.6 |
| 140 | 91.9 | 18.3 | 26.2 |

The increase in $[Ca^{2+}]_i$ has been well known as one of the cellular changes induced by S1P. As described in the above, an increase in $[Ca^{2+}]_i$ caused by S1P stimuli was suppressed by the arylamidrazone derivative of the present invention in CHO-K1 cells which stably express S1P$_3$ receptors. In contrast, in the CHO-K1 cells which stably express S1P$_1$ or S1P$_2$ receptors, an increase in $[Ca^{2+}]_i$ caused by S1P stimuli was not suppressed at all or almost at all by the representative compounds of the present invention. These results indicate that the compound of the present invention suppresses an increase in $[Ca^{2+}]_i$ caused by S1P in an S1P$_3$ receptor subtype-selective manner.

Test Example 2

Effect on the Coronary Blood Flow Rate in Isolated Heart of Rat

A male SD rat weighing about 350 g was anesthetized with pentobarbital sodium (50 mg/kg), and heparin (1000 U/kg) was administered through the lower limb vein. The heart was rapidly isolated and connected to a Langendorff perfusion apparatus. As for the perfusion, constant pressure perfusion was performed at 70±5 mmHg using a Krebs-Henseleit solution (NaCl: 113.8 mmol/L, NaHCO$_3$: 22.0 mmol/L, KCl: 4.7 mmol/L, KH$_2$PO$_4$: 1.2 mmol/L, MgSO$_4$: 1.1 mmol/L, CaCl$_2$: 2.5 mmol/L, glucose: 11.0 mmol/L, sodium pyruvate: 2.0 mmol/L). The temperature of the perfusion solution was set at 37±0.2° C., and gassed with a gas mixture (95% O$_2$ and 5% CO$_2$) such that the oxygen partial pressure was 550 mmHg or more. The coronary perfusion flow rate was measured with an electromagnetic blood flow meter through a probe installed in the circulation pathway. Furthermore, the effects on the heart function were investigated using the left ventricular developed pressure (LVDP), the first derivative of the left ventricular pressure (LV±dp/dt) and the heart rate (HR) as indices. The LVDP was determined by subtracting the left ventricular end diastolic pressure (LVEDP) from the left ventricular systolic pressure (LVSP), which was detected with a latex balloon inserted into the left ventricle, and measured with a pressure strain meter via a pressure transducer. The LVEDP was set to an initial value of 5 to 10 mmHg by adjusting the volume of the latex balloon. Signals measured with the pressure strain meter were conducted to a differential meter and a heart rate meter, to measure the first derivative of the left ventricular pressure (LV±dp/dt) and the heart rate (HR).

The effects of S1P on the coronary blood flow rate and the heart function were evaluated at a concentration of $10^{-9}$ M to $10^{-7}$ M based on the perfusion solution. After stabilization under normal perfusion condition for about 20 minutes, a drug or a solvent was continuously infused into the circulation for 5 minutes. To evaluate the effects of the compound of the present invention on the changes in the coronary blood flow rate induced by S1P, the test compound (Example Compound 33) was continuously infused to the perfusion solution from 5 minutes before the administration of S1P, at a concentration of $10^{-7}$ M.

S1P significantly decreased the coronary blood flow rate at a concentration of $10^{-9}$ M to $10^{-7}$ M, but when the compound of the present invention was administered in advance, the decrease was significantly suppressed. Further, the coronary blood flow rate was significantly increased by administering the compound of the present invention.

Test Example 3

Effects on Hemodynamics in Rat

As for the rat blood pressure and heart rate, the systolic blood pressure (SBP) and the heart rate (HR) were measured with anon-preheating, non-invasive blood pressure manometer for rats and mice. The measurement was performed five times for one time point of measurement. From five data, the highest and the lowest SBP data were excluded, and the integer of the average value of remaining three data sets was taken as the blood pressure or heart rate at the time point of measurement.

The blood pressure and the heart rate were measured over time, 1 hour before the administration of the compound, at 0 hour (immediately before the administration), and 1, 2, 3, 4, 5, 6 and 24 hours after the administration. Five rats were used for each group. The test compound (Example Compound 33; 10 and mg/kg) was orally administered, while the solvent was orally administered for the control group.

As a result, the compound of the present invention did not show any obvious effects on the blood pressure and heart rate of the rats.

Test Example 4

Effect of Compound of the Present Invention on Hemodynamic Changes Caused by FTY720

FTY720, which is known as an immunosuppressant, is reported to cause asymptomatic bradycardia, and it is suggested that this bradycardia is based on the S1P$_3$ receptor agonistic action of FTY720 (Journal of the American Society of Nephrology, 13 (4), 1073-1083 (2002), Bioorganic &medicinal Chemistry Letters, 14, 3501-3505 (2004)). Thus, the effects of the compound of the present invention on the FTY720-induced bradycardia were examined.

A rat was anesthetized with pentobarbital (50 mg/kg, intraperitoneal administration), and then catheters for drug administration and blood pressure measurement were inserted into the lower limb vein and the carotid artery, respectively. The blood pressure was measured with a strain pressure amplifier via a pressure transducer. The heart rate was measured with a tachometer by means of the electrocardiographic wave. The FTY720 used was purchased from Cayman Chemical Co.

FTY720 (1 mg/kg) was intravenously administered, and the effects thereof on hemodynamics were investigated by measuring the blood pressure and the heart rate at 0 minute (immediately before administration), and 10, 20 and 30 minutes immediately after the intravenous administration. The effect of the test compound (Compound 33; 10 and 30 mg/kg) on the hemodynamic changes caused by intravenous administration of FTY720 (1 mg/kg) was evaluated by orally administering the test compound (10 and 30 mg/kg) 4 hours before the intravenous administration of FTY720 (1 mg/kg), since the time to reach the maximum blood concentration for the test compound in oral administration (1 mg/kg) is 4 hours after administration.

As a result, FTY720 reduced the heart rate and induced bradycardia in rats, whereas, which was suppressed in the group administered with the compound of the present invention.

Formulation Example 1

Production of Tablets

Five grams of Compound 33, 125 g of lactose, 40 g of corn starch and 20 g of crystalline cellulose were mixed, and 6 g of hydroxypropylcellulose was added thereto in the form of a 10% ethanol solution. The mixture was subjected to kneading granulation, and extruded through a screen having a diameter of 8 mm to produce granules. The granules were dried, then 4 g of magnesium stearate was added. The resulting mixture was compression molded to produce tablets each having a weight of 200 mg and containing 5 mg of the Compound 33.

Formulation Example 2

Production of Injection Preparation or Liquid Preparation 50 mg of Compound 33 and 900 mg of sodium chloride were dissolved using 90 mL of water for injection, and then the mixture was adjusted to pH 7.0 with 0.1 mmol/L of sodium hydroxide. Water for injection was further used to obtain a total volume of 100 mL. This solution was aseptically filtered, and then filled in glass ampoules in an amount of 2 mL each, to thus produce an injection preparation (liquid preparation) containing 1 mg of the Compound 33 in each ampoule.

Formulation Example 3

Production of Suppository

Witepsol H-15 was heated to melt, and Compound 33 was added thereto to a concentration of 10 mg/mL. The resulting mixture was homogenized. The mixture was filled into plastic containers for suppository in an amount of 2 mL each, and cooled to produce a suppository containing 20 mg of the Compound 33 in each preparation.

Formulation Example 4

Production of Eye Drop 50 mg of Compound 33, 0.1 g of sodium dihydrogen phosphate.dihydrate, 0.9 g of sodium chloride, and 5 mg of benzalkonium chloride were dissolved in 80 mL of purified water, and a 0.1 mol/L aqueous solution of sodium hydroxide was added to adjust the mixture to pH 7.0. Purified water was added thereto to obtain a total volume of 100 mL. The solution was aseptically filtered, and then filled into polypropylene eye dropper bottles in an amount of 5 mL each, to produce an eye drop containing the Compound 33 at a concentration of 0.05%.

The invention claimed is:

1. An arylamidrazone compound represented by formula (1):

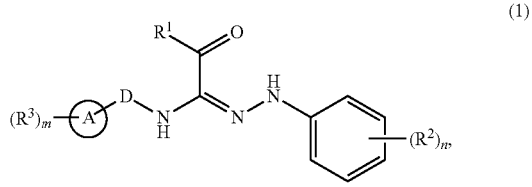

(1)

wherein:
$R^1$ is selected from the group consisting of an n-butyl group, a tert-butyl group, a 1-ethylpropyl group, and a 2,2-dimethylpropyl group, which may be substituted with a halogen atom, a $C_1$-$C_8$ alkoxy group; a phenyl group which may be substituted; a 5- to 7-membered aromatic heterocyclic group; a $C_2$-$C_8$ alkoxy group which may be substituted; or —$NR^4R^5$,
wherein $R^4$ and $R^5$, which are identical or different, each represent a hydrogen atom or a lower alkyl group which may be substituted, or $R^4$ and $R^5$ may be joined with the adjacent nitrogen atom to form a nitrogen-containing heterocyclic ring which may be substituted;
$R^2$ and $R^3$, which are identical or different, each represent a hydrogen atom, a halogen atom, a halo-lower alkyl group, a lower alkyl group, a lower alkynyl group, a lower alkoxy group, a cyano group, a lower alkanoyl group or a lower alkylsulfonyl group;
A represents a benzene ring or a heterocyclic ring;
D represents a single bond or methylene;
m represents an integer from 1 to 3; and
n represents an integer from 1 to 5,
with the proviso that where $R^1$ is an ethoxy group, $R^2$ is a 2,4-dichloro group, $R^3$ is a hydrogen atom, A is a benzene ring, and D is methylene;
where $R^1$ is an ethoxy group, $R^2$ is a 2,4-dichloro group, $R^3$ is a hydrogen atom, a 2-methyl group, a 4-methyl group, a 4-methoxy group or a 4-ethoxy group, A is a benzene ring, and D is a single bond,
where $R^1$ is a phenyl, $R^2$ is hydrogen, D is a single bond, A is a benzene ring, and $R^3$ is a methyl group, and
where $R^1$ is a phenyl group, $R^2$ is a hydrogen, D is a single bond, A is a benzene ring and $R^3$ is a hydrogen atom are excluded,
or a pharmaceutically acceptable salt thereof.

2. An arylamidrazone compound represented by formula (1a):

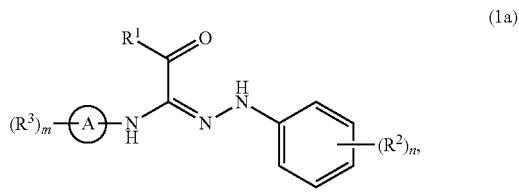

(1a)

wherein:
$R^1$ represents a $C_2$-$C_8$ alkyl group selected from the group consisting of an n-butyl group, a tert-butyl group, a 1-ethylpropyl group, and a 2,2-dimethylpropyl group, which may be substituted with a halogen atom, a $C_1$-$C_8$ alkoxy group; a phenyl group which may be substituted; a 5- to 7-membered aromatic heterocyclic group; a $C_2$-$C_8$ alkoxy group which may be substituted; or —$NR^4R^5$,
wherein $R^4$ and $R^5$, which are identical or different, each represent a hydrogen atom or a lower alkyl group which may be substituted, or $R^4$ and $R^5$ may be joined with the adjacent nitrogen atom to form a nitrogen-containing heterocyclic ring which may be substituted;
$R^2$ and $R^3$, which are identical or different, each represent a hydrogen atom, a halogen atom, a halo-lower alkyl group, a lower alkyl group, a lower alkynyl group, a lower alkoxy group, a cyano group, a lower alkanoyl group or a lower alkylsulfonyl group;
A represents a benzene ring or a heterocyclic ring;
m represents an integer from 1 to 3; and
n represents an integer from 1 to 5,
with the proviso that where $R^1$ is an ethoxy group, $R^2$ is a 2,4-dichloro group, $R^3$ is a hydrogen atom, a 2-methyl group, a 4-methyl group, a 4-methoxy group or a 4-ethoxy group, and A is a benzene ring, where $R^1$ is a phenyl, $R^2$ is hydrogen, A is a benzene ring, and $R^3$ is a methyl group, and
where $R^1$ is a phenyl group, $R^2$ is a hydrogen, A is a benzene ring and $R^3$ is a hydrogen atom is excluded,
or a pharmaceutically acceptable salt thereof.

3. The arylamidrazone compound or the pharmaceutically acceptable salt thereof according to claim 1, wherein $R^1$ is a $C_2$-$C_8$ alkyl group selected from the group consisting of an n-butyl group, a tert-butyl group, a 1-ethylpropyl group, and a 2,2-dimethylpropyl group, which may be substituted with a halogen atom, a $C_1$-$C_8$ alkoxy group; a phenyl group which may be substituted with a halogen atom, a $C_1$-$C_8$ alkyl group, a halo-$C_1$-$C_8$ alkyl group, a $C_1$-$C_8$ alkoxy group; a 5- to 7-membered aromatic heterocyclic group; a $C_2$-$C_8$ alkoxy group which may be substituted with a halogen atom or a $C_1$-$C_8$ alkoxy group; or —$NR^4R^5$ wherein $R^4$ and $R^5$, which are identical or different, each represent a hydrogen atom, or a $C_1$-$C_8$ alkyl group which may be substituted with a halogen atom or a $C_1$-$C_8$ alkoxy group, or $R^4$ and $R^5$ may be joined with the adjacent nitrogen atom to form a nitrogen-containing heterocyclic ring which may be substituted with a halogen atom, a $C_1$-$C_8$ alkyl group, a phenyl group or a $C_1$-$C_8$ alkoxy group; and $R^2$ and $R^3$, which are identical or different, are each a hydrogen atom, a halogen atom, a halo-$C_1$-$C_8$ alkyl group, a $C_1$-$C_8$ alkyl group, a $C_2$-$C_6$ alkynyl group, a $C_1$-$C_8$ alkoxy group, a cyano group, a $C_2$-$C_6$ alkanoyl group or a $C_1$-$C_8$ alkylsulfonyl group.

4. The arylamidrazone compound or the pharmaceutically acceptable salt thereof according to claim 1, wherein $R^1$ is a straight-chained or branched $C_2$-$C_6$ alkyl group selected from the group consisting of an n-butyl group, a tert-butyl group, a 1-ethylpropyl group, and a 2,2-dimethylpropyl group, which may be substituted with a halogen atom, a $C_1$-$C_8$ alkoxy group, or a 5- to 7-membered aromatic heterocyclic group.

5. The arylamidrazone compound or the pharmaceutically acceptable salt thereof according to claim 1, wherein $R^1$ is an n-butyl group, a tert-butyl group, a 1-ethylpropyl group, a 2,2-dimethylpropyl group, or a furyl group.

6. The arylamidrazone compound or the pharmaceutically acceptable salt thereof according to claim 1, wherein $R^2$ and $R^3$, which are identical or different, are a hydrogen atom, a halogen atom, a straight-chained $C_1$-$C_8$ alkyl group, or a $C_2$-$C_6$ alkynyl group, wherein the substitution position thereof is the meta-position or the para-position.

7. The arylamidrazone compound or the pharmaceutically acceptable salt thereof according to claim 1, wherein $R^2$ and $R^3$, which are identical or different, are each a hydrogen atom, a halogen atom, a methyl group or an ethynyl group, wherein the substitution position thereof is the meta-position or the para-position.

8. The arylamidrazone compound or the pharmaceutically acceptable salt thereof according to claim 1, wherein A is a benzene ring, a pyridine ring, a quinoline ring or an isoquinoline ring.

9. An arylamidrazone compound or a pharmaceutically acceptable salt thereof, which is selected from the group consisting of:
- 1-(4-chlorophenylhydrazono)-1-(3-fluorophenylamino)-3,3-dimethyl-2-butanone,
- 1-(4-chlorophenylamino)-1-(4-chlorophenylhydrazono)-3,3-dimethyl-2-butanone,
- 1-(4-chlorophenylhydrazono)-1-(3,5-difluorophenylamino)-3,3-dimethyl-2-butanone,
- 1-(4-chlorophenylhydrazono)-1-(3,5-dichlorophenylamino)-3,3-dimethyl-2-butanone,
- 1-(4-chlorophenylhydrazono)-1-(3,4-dichlorophenylamino)-3,3-dimethyl-2-butanone,
- 1-(3-chlorophenylhydrazono)-1-(3-fluorophenylamino)-3,3-dimethyl-2-butanone,
- 1-(4-chlorophenylamino)-1-(3-chlorophenylhydrazono)-3,3-dimethyl-2-butanone,
- 1-(3-chlorophenylhydrazono)-1-(3,5-dichlorophenylamino)-3,3-dimethyl-2-butanone,
- 1-(3-chlorophenylhydrazono)-1-(3,4-dichlorophenylamino)-3,3-dimethyl-2-butanone,
- 1-(3-fluorophenylamino)-1-(phenylhydrazono)-3,3-dimethyl-2-butanone,
- 1-(4-chlorophenylamino)-1-(phenylhydrazono)-3,3-dimethyl-2-butanone,
- 1-(3,5-dichlorophenylamino)-1-(phenylhydrazono)-3,3-dimethyl-2-butanone,
- 1-(3,4-dichlorophenylamino)-1-(phenylhydrazono)-3,3-dimethyl-2-butanone,
- 1-(3-fluorophenylamino)-1-(4-fluorophenylhydrazono)-3,3-dimethyl-2-butanone,
- 1-(4-fluorophenylamino)-1-(4-fluorophenylhydrazono)-3,3-dimethyl-2-butanone,
- 1-(4-chlorophenylamino)-1-(4-fluorophenylhydrazono)-3,3-dimethyl-2-butanone,
- 1-(4-bromophenylamino)-1-(4-fluorophenylhydrazono)-3,3-dimethyl-2-butanone,
- 1-(3,5-dichlorophenylamino)-1-(4-fluorophenylhydrazono)-3,3-dimethyl-2-butanone,
- 1-(3,4-dichlorophenylamino)-1-(4-fluorophenylhydrazono)-3,3-dimethyl-2-butanone,
- 1-(3-fluorophenylamino)-1-(4-methylphenylhydrazono)-3,3-dimethyl-2-butanone,
- 1-(4-chlorophenylamino)-1-(4-methylphenylhydrazono)-3,3-dimethyl-2-butanone,
- 1-(4-methylphenylamino)-1-(4-methylphenylhydrazono)-3,3-dimethyl-2-butanone,
- 1-(3,5-dichlorophenylamino)-1-(4-methylphenylhydrazono)-3,3-dimethyl-2-butanone,
- 1-(3,4-dichlorophenylamino)-1-(4-methylphenylhydrazono)-3,3-dimethyl-2-butanone,
- 1-(4-bromophenylhydrazono)-1-(3-fluorophenylamino)-3,3-dimethyl-2-butanone,
- 1-(4-bromophenylhydrazono)-1-(4-fluorophenylamino)-3,3-dimethyl-2-butanone,
- 1-(4-bromophenylhydrazono)-1-(4-chlorophenylamino)-3,3-dimethyl-2-butanone,
- 1-(4-bromophenylamino)-1-(4-bromophenylhydrazono)-3,3-dimethyl-2-butanone,
- 1-(4-bromophenylhydrazono)-1-(4-ethynylphenylamino)-3,3-dimethyl-2-butanone,
- 1-(4-bromophenylhydrazono)-1-(3,5-dichlorophenylamino)-3,3-dimethyl-2-butanone,
- 1-(4-bromophenylhydrazono)-1-(3,4-dichlorophenylamino)-3,3-dimethyl-2-butanone,
- 1-(3,4-dichlorophenylhydrazono)-1-(3-fluorophenylamino)-3,3-dimethyl-2-butanone,
- 1-(4-bromophenylhydrazono)-1-(4-chloro-3-fluorophenylamino)-3,3-dimethyl-2-butanone,
- 1-(4-chlorophenylamino)-1-(4-ethynylphenylhydrazono)-3,3-dimethyl-2-butanone,
- 1-(3,4-dichlorophenylhydrazono)-1-(3-ethynylphenylamino)-3,3-dimethyl-2-butanone,
- 1-(3-chlorophenylamino)-1-(4-ethynylphenylhydrazono)-3,3-dimethyl-2-butanone,
- 1-(4-chlorophenylhydrazono)-1-(3,4-dichlorophenylamino)-2-hexanone,
- 1-(4-chlorophenylamino)-1-(4-chlorophenylhydrazono)-3-ethyl-2-pentanone,
- 1-(4-chlorophenylhydrazono)-1-(4-ethynylphenylamino)-2-hexanone,
- 1-(4-chlorophenylhydrazono)-1-(4-fluorophenylamino)-3-ethyl-2-pentanone,
- 1-(4-chlorophenylhydrazono)-1-(3-fluorophenylamino)-4,4-dimethyl-2-pentanone,
- 1-(4-chlorophenylhydrazono)-1-(4-fluorophenylamino)-4,4-dimethyl-2-pentanone,
- 1-(4-chlorophenylamino)-1-(4-chlorophenylhydrazono)-2-hexanone,
- 1-(4-chlorophenylamino)-1-(4-chlorophenylhydrazono)-2-(2-furyl)-2-ethanone,
- 1-(4-chlorophenylhydrazono)-1-(4-ethynylphenylamino)-2-(2-furyl)-2-ethanone,
- 1-(4-chlorophenylhydrazono)-1-(4-fluorophenylamino)-2-(2-furyl)-2-ethanone,
- 1-(4-bromophenylamino)-1-(4-chlorophenylhydrazono)-2-(2-furyl)-2-ethanone, 4-chloro-1-(4-chlorophenylhydrazono)-1-(4-ethynylphenylamino)-3,3-dimethyl-2-butanone, 1-(3-chlorophenylamino)-1-(3,4-dichlorophenylhydrazono)-3,3-dimethyl-2-butanone, 1-(4-chlorophenylamino)-1-(3,4-dichlorophenylhydrazono)-3,3-dimethyl-2-butanone, 1-(3-fluorophenylamino)-1-(4-ethynylphenylhydrazono)-3,3-dimethyl-2-butanone, 1-(3,4-dichlorophenylhydrazono)-1-(4-ethynylphenylamino)-3,3-dimethyl-2-butanone, 1-(3-chlorophenylamino)-1-(4-chlorophenylhydrazono)-3,3-dimethyl-2-butanone, 1-(4-bromophenylamino)-1-(4-chlorophenylhydrazono)-3,3-dimethyl-2-butanone, 1-(4-chloro-3-fluorophenylamino)-1-(4-chlorophenylhydrazono)-3,3-dimethyl-2-butanone, 1-(4-chlorophenylhydrazono)-1-(4-ethynylphenylamino)-3,3-dimethyl-2-butanone, 1-(3-chlorophenylamino)-1-(4-chlorophenylhydrazono)-3-ethyl-2-pentanone, 1-(4-ethynylphenylamino)-1-(4-ethynylphenylhydrazono)-3,3-dimethyl-2-butanone, 1-(4-chlorophenylamino)-1-(4-chlorophenylhydrazono)-4,4-dimethyl-2-pentanone, 1-(3-chlorophenylamino)-1-(4-chlorophenylhydrazono)-4,4-dimethyl-2-pentanone, and 1-(3-chlorophenylamino)-1-(4-chlorophenylhydrazono)-2-hexanone.

10. A composition, comprising the arylamidrazone compound or the pharmaceutically acceptable salt thereof according to claim 1 and a pharmaceutically acceptable carrier.

11. The composition according to claim 10, which is a pharmaceutical composition for the treatment of angina pectoris or myocardial infarction caused by coronary spasm, or bradycardia.

12. A method of manufacturing a medicine, comprising adding the arylamidrazone compound or the pharmaceutically acceptable salt thereof according to claim 1 to a pharmaceutically acceptable carrier.

13. A method for treating angina pectoris caused by coronary spasm, myocardial infarction caused by coronary spasm, or bradycardia, each of which is caused by $S1P_3$ receptor stimulation wherein the method comprises administering an effective amount of the arylamidrazone compound or the pharmaceutically acceptable salt thereof according to claim 1 to a subject in need thereof.

14. The arylamidrazone compound or the pharmaceutically acceptable salt thereof according to claim 2, wherein $R^1$ is a $C_2$-$C_8$ alkyl group selected from the group consisting of an n-butyl group, a tert-butyl group, a 1-ethylpropyl group, and a 2,2-dimethylpropyl group which may be substituted with a halogen atom or a $C_1$-$C_8$ alkoxy group; a phenyl group which may be substituted with a halogen atom, a $C_1$-$C_8$ alkyl group, a halo-$C_1$-$C_8$ alkyl group, a $C_1$-$C_8$ alkoxy group; a 5- to 7-membered aromatic heterocyclic group; a $C_2$-$C_8$ alkoxy group which may be substituted with a halogen atom; a $C_1$-$C_8$ alkoxy group; or —$NR^4R^5$ (wherein $R^4$ and $R^5$, which are identical or different, each represent a hydrogen atom, or a $C_1$-$C_8$ alkyl group which may be substituted with a halogen atom or a $C_1$-$C_8$ alkoxy group, or $R^4$ and $R^5$ may be joined with the adjacent nitrogen atom to form a nitrogen-containing heterocyclic ring which may be substituted with a halogen atom, a $C_1$-$C_8$ alkyl group, a phenyl group or a $C_1$-$C_8$ alkoxy group; and $R^2$ and $R^3$, which are identical or different, are each a hydrogen atom, a halogen atom, a halo-$C_1$-$C_8$ alkyl group, a $C_1$-$C_8$ alkyl group, a $C_2$-$C_6$ alkynyl group, a $C_1$-$C_8$ alkoxy group, a cyano group, a $C_2$-$C_6$ alkanoyl group or a $C_1$-$C_8$ alkylsulfonyl group.

15. The arylamidrazone compound or the pharmaceutically acceptable salt thereof according to claim 2, wherein $R^1$ is a straight-chained or branched $C_2$-$C_6$ alkyl group selected from the group consisting of an n-butyl group, a tert-butyl group, a 1-ethylpropyl group, and a 2,2-dimethylpropyl group, which may be substituted with a halogen atom a $C_{1-8}$ alkoxy group; or a 5- to 7-membered aromatic heterocyclic group.

16. The arylamidrazone compound or the pharmaceutically acceptable salt thereof according to claim 2, wherein $R^1$ is an n-butyl group, a tert-butyl group, a 1-ethylpropyl group, a 2,2-dimethylpropyl group, or a furyl group.

17. The method according to claim 13, comprising treating angina pectoris caused by coronary spasm.

18. The method according to claim 13, comprising treating myocardial infarction caused by coronary spasm.

19. The method according to claim 13, comprising treating bradycardia.

\* \* \* \* \*